United States Patent
Mueller et al.

(10) Patent No.: US 12,391,947 B2
(45) Date of Patent: Aug. 19, 2025

(54) MODULATION OF SPTLC1 VIA RECOMBINANT ADENO-ASSOCIATED VECTORS

(71) Applicant: University of Massachusetts, Boston, MA (US)

(72) Inventors: Christian Mueller, Worcester, MA (US); Gabriela Toro Cabrera, Worcester, MA (US); Robert H. Brown, Jr., Worcester, MA (US)

(73) Assignee: University of Massachusetts, Westborough, MA (US)

( * ) Notice: Subject to any disclaimer, the term of this patent is extended or adjusted under 35 U.S.C. 154(b) by 1036 days.

(21) Appl. No.: 17/297,521

(22) PCT Filed: Nov. 27, 2019

(86) PCT No.: PCT/US2019/063558
§ 371 (c)(1),
(2) Date: May 27, 2021

(87) PCT Pub. No.: WO2020/112967
PCT Pub. Date: Jun. 4, 2020

(65) Prior Publication Data
US 2022/0033824 A1      Feb. 3, 2022

Related U.S. Application Data

(60) Provisional application No. 62/772,668, filed on Nov. 29, 2018.

(51) Int. Cl.
| | |
|---|---|
| *C12N 15/113* | (2010.01) |
| *A61K 35/761* | (2015.01) |
| *C12N 15/10* | (2006.01) |
| *C12N 15/86* | (2006.01) |

(52) U.S. Cl.
CPC ........ *C12N 15/1137* (2013.01); *A61K 35/761* (2013.01); *C12N 15/102* (2013.01); *C12N 15/86* (2013.01); *C12N 2310/141* (2013.01); *C12N 2310/531* (2013.01); *C12N 2750/14133* (2013.01); *C12N 2750/14143* (2013.01); *C12Y 203/0105* (2013.01)

(58) Field of Classification Search
CPC ............... C12N 15/1137; C12N 15/86; C12N 2310/141; C12N 2310/531; C12N 2750/14133; C12N 2750/14143; C12N 15/102; C12Y 203/0105; A61K 35/761
See application file for complete search history.

(56) References Cited

U.S. PATENT DOCUMENTS

| | | | |
|---|---|---|---|
| 2010/0186103 A1 | 7/2010 | Gao et al. | |
| 2012/0252881 A1* | 10/2012 | Ochiya ................. | A61K 31/713 514/44 R |
| 2013/0184217 A1* | 7/2013 | Chau .................... | A61K 31/713 435/375 |

FOREIGN PATENT DOCUMENTS

| | | | | |
|---|---|---|---|---|
| WO | WO 2008/006007 A2 | 1/2008 | | |
| WO | WO-2014011975 A2 * | 1/2014 | ......... | A61K 31/7088 |
| WO | WO 2016/172008 A1 | 10/2016 | | |
| WO | WO 2017/153753 A1 | 9/2017 | | |
| WO | WO 2018/057855 A1 | 3/2018 | | |
| WO | WO-2020038973 A1 * | 2/2020 | ......... | C12N 15/1137 |

OTHER PUBLICATIONS

Jarald et al., "Nucleic acid drugs: a novel approach", African Journal of Biotechnology vol. 3, Published Dec. 2004, pp. 662-666. ( Year: 2004).*
Hojjati et al., "Serine palmitoyl-CoA transferase (SPT) deficiency and sphingolipid levels in mice", Biochimica et Biophysica Acta, Published 2005, pp. 44-51. (Year: 2005).*
PCT/US2019/063558, Mar. 10, 2020, International Search Report and Written Opinion.
PCT/US2019/063558, Jun. 10, 2021, International Preliminary Report on Patentability.
International Search Report and Written Opinion for Application No. PCT/US2019/063558, mailed Mar. 10, 2020.
International Preliminary Report on Patentability for Application No. PCT/US2019/063558, mailed Jun. 10, 2021.
Geekiyanage et al., MicroRNA-137/181c regulates serine palmitoyltransferase and in turn amyloid β, novel targets in sporadic Alzheimer's disease. J Neurosci. Oct. 12, 2011;31(41):14820-30. doi: 10.1523/JNEUROSCI.3883-11.2011.
Huang et al., Identification of miR-145 targets through an integrated omics analysis. Mol Biosyst. Jan. 2015;11(1):197-207. doi: 10.1039/c4mb00585f. Epub Oct. 30, 2014. Author Manuscript. 21 pages.
Lamari et al., Disorders of phospholipids, sphingolipids and fatty acids biosynthesis: toward a new category of inherited metabolic diseases. J Inherit Metab Dis. May 2013;36(3):411-25. doi: 10.1007/s10545-012-9509-7. Epub Jul. 20, 2012.
Penno et al., Hereditary sensory neuropathy type 1 is caused by the accumulation of two neurotoxic sphingolipids. J Biol Chem. Apr. 9, 2010;285(15):11178-87. doi: 10.1074/jbc.M109.092973. Epub Jan. 22, 2010.
Ruangsiriluk et al., Silencing of enzymes involved in ceramide biosynthesis causes distinct global alterations of lipid homeostasis and gene expression. J Lipid Res. Aug. 2012;53(8):1459-71. doi: 10.1194/jlr.M020941. Epub May 23, 2012.

\* cited by examiner

*Primary Examiner* — Abigail Vanhorn
*Assistant Examiner* — Stephanie L Sullivan
(74) *Attorney, Agent, or Firm* — Wolf, Greenfield & Sacks, P.C.

(57) ABSTRACT

The disclosure provides, in some aspects, compositions (e.g., isolated nucleic acids and rAAVs) comprising a transgene which encodes at least one inhibitory nucleic acid which decreases expression of a gene encoding a serine palmitoyltransferase protein (e.g., SPTLC1). In some aspects, the disclosure relates to methods of treating hereditary sensory and autonomic neuropathy 1 (HSAN1) by administering the compositions described by the disclosure to a cell or subject.

9 Claims, 4 Drawing Sheets
Specification includes a Sequence Listing.

MODULATION OF SPTLC1 VIA RECOMBINANT ADENO-ASSOCIATED VECTORS

RELATED APPLICATION

This Application is a national stage filing under 35 U.S.C. § 371 of international application PCT/US2019/063558, filed Nov. 27, 2019, which claims priority under 35 U.S.C. § 119(e) to U.S. provisional patent application Ser. No. 62/772,668, filed Nov. 29, 2018, the entire contents of each of which are incorporated herein by reference.

REFERENCE TO AN ELECTRONIC SEQUENCE LISTING

The contents of the electronic sequence listing (U012070110US01-SEQ-KZM.txt; Size: 22,203 bytes; and Date of Creation: May 27, 2021) is herein incorporated by reference in its entirety.

BACKGROUND

Hereditary sensory and autonomic neuropathy 1 (HSAN1) is an autosomal dominant disease characterized by progressive degeneration of dorsal root ganglion and motor neurons by causing a large loss of myelinated fibers. HSAN1 typically leads to distal sensory loss including temperature sensation in the hands and feet, skin ulcers and infections, and muscle weakening and atrophy. If distal sensory loss goes untreated and ulcerations develop, limb amputation can occur. HSAN1 is a rare condition, with an estimated global incidence of 1 case per 1,000,000 subjects.

SUMMARY

Aspects of the disclosure relate to compositions and methods useful for treating diseases and disorders associated with dysfunction or aberrant (e.g., increased or decreased) expression of the SPTLC1 subunit of serine palmitoyltransferase (SPT), for example Hereditary sensory and autonomic neuropathy 1 (HSAN1). SPT catalyzes the formation of serine palmitoyl-CoA, a key intermediate in the formation of sphingolipids. In some instances, mutations in SPTLC1 alter substrate specificity resulting in two atypical deoxy-sphingoid bases (DSBs), which cannot be converted or degraded. Therefore, these bases accumulate in cells, becoming neurotoxic. In some embodiments, mutations of a SPTLC1 protein include C133W, which results in increased SPT activity; C133Y, V144D, and A352V, which result in decreased SPT activity; and S331F, which results in decreased SPT activity, wherein the SPTLC1 reference protein comprises SEQ ID NO: 24. In some embodiments, mutations of SPTLC1 are associated with severe HSAN1 symptoms. The disclosure is based, in part, on inhibitory nucleic acids (e.g., vectors, such as viral vectors, encoding one or more inhibitory nucleic acids) that silence expression of SPTLC1 (e.g., mutant SPTLC1), thereby reducing the production of the toxic DSBs in a cell or a subject.

Accordingly, in some aspects, the disclosure provides an isolated nucleic acid comprising a transgene encoding at least one inhibitory nucleic acid, wherein the at least one inhibitory nucleic acid reduces expression of a gene encoding a serine palmitoyltransferase subunit, and wherein the transgene is flanked by adeno-associated virus (AAV) inverted terminal repeats (ITRs).

In some aspects, the disclosure provides a recombinant AAV (rAAV) comprising a nucleic acid comprising (i) a transgene encoding at least one inhibitory nucleic acid that reduces expression of a gene encoding a serine palmitoyltransferase subunit (e.g., SPTLC1) and that is flanked by inverted terminal repeats (ITRs) derived from adeno-associated virus (AAV), and (ii) at least one capsid protein.

In some embodiments, an isolated nucleic acid or rAAV further comprises a second transgene. In some embodiments, the second transgene encodes a therapeutic protein, a selectable marker protein, or a reporter protein. In some embodiments, a therapeutic protein is a wild-type serine palmitoyltransferase subunit (e.g., comprising amino acid sequence of SEQ ID NO: 24). In some embodiments, a selectable marker is selected from the group consisting of: ampicillin resistance, neomycin resistance, geneticin resistance, and hygromycin resistance. In some embodiments, a reporter protein is selected from the group consisting of GFP, YFP, RFP, beta-galactosidase, or Luciferase.

In some embodiments, a transgene encoding at least one inhibitory nucleic acid is located upstream of the second transgene. In some embodiments, the second transgene is located upstream of a transgene encoding the at least one inhibitory nucleic acid.

In some embodiments, an inhibitory nucleic acid is a microRNA, an artificial microRNA (amiRNA), a shRNA, a siRNA, or an antisense oligonucleotide (ASO). In some embodiments, at least one inhibitory nucleic acid is encoded by a sequence comprising at least 6 (e.g., 6, 7, 8, 9, 10, 11, 12, 13, 14, 15, 16, 17, 18, 19, 20, 21, or more) contiguous nucleotides as set forth in SEQ ID NOs: 1-6. In some embodiments, at least one inhibitory nucleic acid binds a target sequence comprising at least 6 (e.g., 6, 7, 8, 9, 10, 11, 12, 13, 14, 15, 16, 17, 18, 19, 20, 21, or more) contiguous nucleotides as set forth in SEQ ID NOs: 10-15. In some embodiments, at least one inhibitory nucleic acid is encoded by a sequence comprising at least 6 (e.g., 6, 7, 8, 9, 10, 11, 12, 13, 14, 15, 16, 17, 18, 19, 20, 21, or more) contiguous nucleotides as set forth in SEQ ID NOs: 16-21.

In some embodiments, a transgene encodes one inhibitory nucleic acid. In some embodiments, a transgene encodes more than one, for example, two, three, four, five, or more (e.g., 6, 7, 8, 9, or 10) inhibitory nucleic acids.

In some embodiments, an isolated nucleic acid sequence encoding a transgene (e.g., a transgene encoding one or more inhibitory nucleic acids, a transgene encoding one or more selectable markers or reporter proteins, a transgene encoding a therapeutic protein, for example SPTLC1, etc.) is operably linked to a promoter. In some embodiments, a promoter is a constitutive promoter. In some embodiments, a promoter is an inducible promoter. In some embodiments, a promoter is a tissue-specific promoter. In some embodiments, the promoter is an RNA pol III promoter (e.g., U6, H1, etc.), an RNA pol II promoter, a chicken beta-actin (CB) promoter, a synapsin promoter.

In some embodiments, a transgene encoding at least one inhibitory nucleic acid is located in an untranslated region such as an intron, a 5' untranslated region (5'UTR), or a 3' untranslated region (3'UTR) of an isolated nucleic acid.

In some embodiments, an rAAV comprises a capsid protein having a serotype selected from the group consisting of: AAV1, AAV2, AAV3, AAV4, AAV5, AAV6, AAV7, AAV8, AAVrh8, AAV9, AAV10, AAVrh10, and AAV.PHPB.

In some aspects, the disclosure provides a kit comprising a container housing an isolated nucleic acid or an rAAV as described herein. In some embodiments, a kit further comprises a pharmaceutically acceptable carrier. In some embodiments, the isolated nucleic or the rAAV and the pharmaceutically acceptable carrier are housed in the same container. In some embodiments, the container is a syringe.

In some aspects, the disclosure provides a host cell comprising an isolated nucleic acid or the rAAV as described herein. In some embodiments, a host cell is a eukaryotic cell. In some embodiments, a host cell is a mammalian cell.

In some aspects, the disclosure provides a method of decreasing expression of a target gene in a cell or a subject, wherein an isolated nucleic acid or rAAV as described herein is administered to the cell or the subject. In some embodiments, a target gene is a SPTLC1 gene. In some embodiments, a SPTCL1 gene comprises SEQ ID NO: 22 or 23. In some embodiments, a target gene comprises one or more mutations (e.g., 2, 3, 4, 5, 6, 7,8,9, 10, or more mutations). In some embodiments a target gene is a SPTLC1 gene that encodes a SPTCL1 protein having one or more of the following mutations: C133W, C133Y, V144D, S331F, and A352V, optionally wherein the SPTLC1 reference protein comprises SEQ ID NO: 24.

In some embodiments, administration of an isolated nucleic acid or an rAAV results in target gene expression (e.g., SPTLC1 expression) that is decreased by at least 2-fold, at least 10-fold, at least 20-fold, at least 30-fold, at least 40-fold, at least 50-fold, at least 60-fold, at least 70-fold, at least 80-fold, at least 90-fold, or at least 100-fold relative to expression of the target gene (e.g., SPTLC1) in the cell or subject prior to administration. In some embodiments, administration of an isolated nucleic acid or an rAAV results in target gene expression (e.g., SPTLC1 expression) that is decreased by at least 2-fold, at least 10-fold, at least 20-fold, at least 30-fold, at least 40-fold, at least 50-fold, at least 60-fold, at least 70-fold, at least 80-fold, at least 90-fold, or at least 100-fold relative to a cell or subject that does not contain one or more mutations in the target gene.

In some embodiments, a cell is a neuron. In some embodiments, the neuron is a sensory neuron. In some embodiments, a subject is a mammal, for example a human, non-human primate, dog, cat, pig, mouse, or rat.

In some aspects, the disclosure provides a method of treating hereditary sensory and autonomic neuropathy 1 (HSAN1) in a subject, wherein an isolated nucleic acid or an rAAV as described herein is administered to a subject having or suspected of having HSAN1. In some embodiments, a subject having or suspected of having HSAN1 is characterized by having one or more mutations of the SPTLC1 gene. In some embodiments, the one or more mutations comprises a missense mutation.

In some aspects, the disclosure provides a composition comprising an isolated nucleic acid or rAAV as described by the disclosure. In some embodiments, a composition further comprises a pharmaceutically acceptable carrier.

BRIEF DESCRIPTION OF DRAWINGS

FIG. 1A is an illustration of a plasmid construct, which inverted terminal repeats (ITRs) flanking a transgene encoding a microRNA, a RNA pol III Human H1 promoter operably linked to a transgene, a CMV enhancer/chicken β-actin (CB) promoter operably linked to a transgene encoding green fluorescent protein (GFP) and a poly A tail. FIG. 1B depicts an example of a microRNA sequence, with a 2-8 nucleotide seed sequence labeled. FIG. 1C is an alignment of miR-519 to both hamster and human SPTLC1.

FIG. 2A shows digital PCR data for three biological replicates of different microRNAs targeting both human and hamster SPTLC1 in HEK293T human cells. FIG. 2B shows digital PCR data for three biological replications of different microRNAs targeting both human and hamster SPTLC1 in CHO hamster cells.

DETAILED DESCRIPTION

Figure 1A:
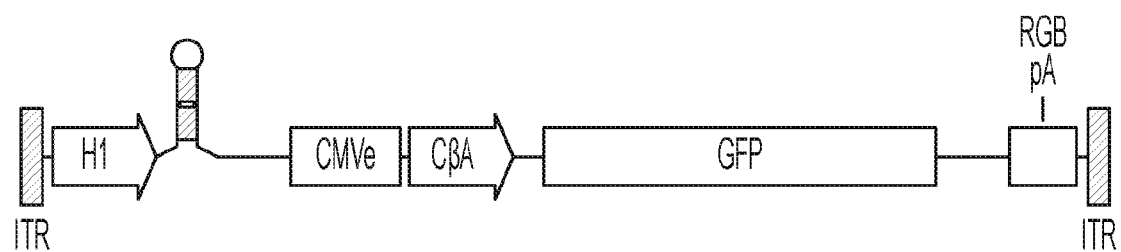
FIGS. 1A-1C depict embodiments of microRNAs that target human SPTLC1, hamster SPTLC1, or both human and hamster SPTLC1.

Aspects of the disclosure relate to methods and compositions for modulating (e.g., decreasing) expression of a target gene (e.g., SPTLC1) in a cell or subject. In some embodiments, the disclosure provides a transgene encoding at least one inhibitory nucleic acid for modulating SPTLC1 gene expression. In some embodiments, the disclosure provides microRNAs which modulate expression of a target gene (e.g., SPTLC1). In some embodiments, the at least one inhibitory nucleic acid is delivered to a cell or a subject in an recombinant adeno-associated virus (rAAV).

In some aspects, the disclosure relates to methods for decreasing expression of a target gene (e.g., SPTLC1) in a cell or subject. In some embodiments, the target gene comprises missense mutations associated with a gain-of-function disorder relative to a normal cell or subject. Therefore, methods and compositions of the disclosure may be utilized, in some embodiments, to treat diseases and disorders associated with gain-of-function disorders of a target gene product, for example, Hereditary sensory and autonomic neuropathy 1 (HSAN1), which typically results from one or more mutations in at least one copy of the SPTLC1 gene. In some embodiments, the one or more mutations lead to a gain-of-function disorder of a serine palmitoyltransferase (SPT) protein.

Transgenes

The disclosure is based, in part, on transgenes encoding inhibitory nucleic acids that decrease expression of a gene encoding a serine palmitoyltransferase (also referred to as a SPT or SPTLC protein), for example SPTLC1. As used herein, "a SPT protein" refers to a serine palmitoyltransferase protein which catalyzes one step in the synthesis of sphingolipids. Sphingolipids are a component of plasma membranes involved in signal transmission, particularly in neurons. Examples of SPT proteins in humans include but are not limited to SPT1, SPT2, and SPT3. In some embodiments, a SPT protein is encoded by SPTLC1, which encodes a serine palmitoyltransferase type 1 subunit. In some embodiments, a SPT protein is encoded by SPTLC2, which encodes a serine palmitoyltransferase type 2 subunit. In some embodiments, a SPT protein is encoded by SPTLC3, which encodes a serine palmitoyltransferase type 3 subunit. In some embodiments, a SPT protein is a combination of SPTLC1, SPTLC2, and/or SPTLC3 proteins. As disclosed herein, a SPT protein can be a portion or a fragment of a SPT protein. In some embodiments, a SPT protein as disclosed herein is a variant of a SPT protein, such as a SPT protein comprising one or more point mutants or a truncated SPT protein (e.g., containing one or fewer bases than a wild-type, non-truncated SPT protein).

In humans, SPTLC1 is encoded by the SPTLC1 gene (Gene ID: 10558, human), which is conserved in chimpanzee, mouse, rat, dog, cow, mouse, rat, and chicken. The SPTLC1 gene in human is ubiquitously expressed in tissues such as nervous, thyroid, gall bladder.

In some embodiments, a SPTLC1 protein is encoded is encoded by a human SPTLC1 gene, which comprises the sequence set forth in NCBI Ref. Seq ID No:

NM_001281303.1, NM_178324.2, or NM_006415.3. In some embodiments, a SPTLC1 protein comprises an amino acid sequence that is 99% identical, 95% identical, 90% identical, 80% identical, 70% identical, 60% identical, or 50% identical to the amino acid sequence encoded by the nucleic acid sequence set forth in any one of NCBI Ref. Seq ID Nos. NM_001281303.1, NM_178324.2, and NM_006415.3.

In some embodiments, a SPTLC1 protein is encoded by a mouse SPTLC1 gene, which comprises the nucleic acid sequence set forth in NCBI Ref Seq ID No: NM_009269.2. In some embodiments, a SPTLC1 protein comprises an amino acid sequence that is 99% identical, 95% identical, 90% identical, 80% identical, 70% identical, 60% identical, or 50% identical to the amino acid sequence encoded by the nucleic acid sequence set forth in NCBI Ref. Seq ID No: NM_009269.2.

In some embodiments, a SPTCL1 gene comprises a nucleic acid sequence that is 99% identical, 95% identical, 90% identical, 80% identical, 70% identical, 60% identical, or 50% identical to the sequence set forth in SEQ ID NO: 22.

In some embodiments, a SPTCL1 gene encodes a protein having an amino acid sequence that is 99% identical, 95% identical, 90% identical, 80% identical, 70% identical, 60% identical, or 50% identical to the sequence set forth in SEQ ID NO: 24.

In some embodiments, a human SPTCL1 protein comprises the amino acid sequence set forth in any one of NCBI Ref. Seq ID No: NP_001268232.1, NP_006406.1, and NP_847894.1. In some embodiments, a SPTLC1 protein comprises an amino acid sequence that is 99% identical, 95% identical, 90% identical, 80% identical, 70% identical, 60% identical, or 50% identical to the amino acid sequence encoded by the nucleic acid sequence set forth in any one of NCBI Ref. Seq ID No: NP_001268232.1, NP_006406.1, and NP_847894.1.

In some embodiments, a SPTLC1 protein comprises an amino acid sequence that is 99% identical, 95% identical, 90% identical, 80% identical, 70% identical, 60% identical, or 50% identical to the amino acid sequence encoded by the nucleic acid sequence set forth in NCBI Ref. Seq ID No: NM_009269.2.

In some embodiments, a mouse SPTCL1 protein comprises the amino acid sequence set forth in NCBI Ref. Seq ID No: NP_033295.2. In some embodiments, a mouse SPTLC1 protein comprises an amino acid sequence that is 99% identical, 95% identical, 90% identical, 80% identical, 70% identical, 60% identical, or 50% identical to the protein encoded by the nucleic acid sequence set forth in SEQ ID NO: 23.

In some embodiments, a SPTCL1 gene encodes a protein having an amino acid sequence that is 99% identical, 95% identical, 90% identical, 80% identical, 70% identical, 60% identical, or 50% identical to the sequence set forth in SEQ ID NO: 25.

A region comprising a transgene (e.g., a first region, a second region, third region, fourth region, etc.) may be positioned at any suitable location of the isolated nucleic acid. The region may be positioned in any untranslated portion of the nucleic acid, including, for example, an intron, a 5' or 3' untranslated region, etc.

In some cases, it may be desirable to position the region (e.g., the second region, third region, fourth region, etc.) upstream of the first codon of a nucleic acid sequence encoding a protein (e.g., a protein coding sequence). For example, the region may be positioned between the first codon of a protein coding sequence) and 2000 nucleotides upstream of the first codon. The region may be positioned between the first codon of a protein coding sequence and 1000 nucleotides upstream of the first codon. The region may be positioned between the first codon of a protein coding sequence and 500 nucleotides upstream of the first codon. The region may be positioned between the first codon of a protein coding sequence and 250 nucleotides upstream of the first codon. The region may be positioned between the first codon of a protein coding sequence and 150 nucleotides upstream of the first codon.

In some cases (e.g., when a transgene lacks an intron), it may be desirable to position the region (e.g., the second region, third region, fourth region, etc.) upstream of the poly-A tail of a transgene. For example, the region may be positioned between the first base of the poly-A tail and 2000 nucleotides upstream of the first base. The region may be positioned between the first base of the poly-A tail and 1000 nucleotides upstream of the first base. The region may be positioned between the first base of the poly-A tail and 500 nucleotides upstream of the first base. The region may be positioned between the first base of the poly-A tail and 250 nucleotides upstream of the first base. The region may be positioned between the first base of the poly-A tail and 150 nucleotides upstream of the first base. The region may be positioned between the first base of the poly-A tail and 100 nucleotides upstream of the first base. The region may be positioned between the first base of the poly-A tail and 50 nucleotides upstream of the first base. The region may be positioned between the first base of the poly-A tail and 20 nucleotides upstream of the first base. In some embodiments, the region is positioned between the last nucleotide base of a promoter sequence and the first nucleotide base of a poly-A tail sequence.

In some cases, the region may be positioned downstream of the last base of the poly-A tail of a transgene. The region may be between the last base of the poly-A tail and a position 2000 nucleotides downstream of the last base. The region may be between the last base of the poly-A tail and a position 1000 nucleotides downstream of the last base. The region may be between the last base of the poly-A tail and a position 500 nucleotides downstream of the last base. The region may be between the last base of the poly-A tail and a position 250 nucleotides downstream of the last base. The region may be between the last base of the poly-A tail and a position 150 nucleotides downstream of the last base.

It should be appreciated that in cases where a transgene encodes more than one miRNA, each miRNA may be positioned in any suitable location within the transgene. For example, a nucleic acid encoding a first miRNA may be positioned in an intron of the transgene and a nucleic acid sequence encoding a second miRNA may be positioned in another untranslated region (e.g., between the last codon of a protein coding sequence and the first base of the poly-A tail of the transgene).

The disclosure is based, in part, on a transgene encoding a therapeutic protein. As used herein, a therapeutic protein is any protein that provides a therapeutic benefit to patients having HSAN1. In some embodiments, a therapeutic protein is a wild-type serine palmitoyltransferase subunit (e.g., comprising amino acid sequence of SEQ ID NO: 24).

The disclosure is based, in part, on a transgene encoding a selectable marker protein or a reporter protein. As used herein, a selectable marker is a gene which has been introduced into a cell to facilitate artificial selection. Artificial selection, as used herein, refers to the division of cells or subjects which possess a desired trait from cells or subjects which do not possess the desired trait. In some embodiments, a selectable marker protein facilitates positive selection, wherein the selectable marker provides an advantage to the cell or subject. In some embodiments, a selectable marker protein facilitates negative selection, wherein the selectable marker protein prohibits growth or survival of the cell or subject. Commonly utilized selectable proteins are antibiotic resistance genes, which allow the host cell or subject to survive in the presence of an antibiotic. Examples of antibiotic selectable markers include ampicillin resistance genes, geneticin resistance genes, hygromycin resistance genes, and neomycin genes.

The disclosure is based, in part, on a transgene encoding a reporter protein. As used herein, a reporter protein is used as an indication of whether a cell or subject comprises an isolated nucleic acid of the present disclosure. Commonly utilized reporter proteins include green fluorescent protein (GFP), red fluorescent protein (RFP), yellow fluorescent protein (YFP), beta-galactosidase, and firefly Luciferase.

In some embodiments, the transgene encodes one inhibitory nucleic acid. In some embodiments, the transgene encodes more than one inhibitory nucleic acids. For example, in some embodiments, a transgene encodes 2, 3, 4, 5, 6, 7, 8, 9, 10, or more inhibitory nucleic acids.

Inhibitory Nucleic Acids

In some aspects, the disclosure relates to isolated nucleic acids and rAAVs comprising a transgene, wherein the transgene is a hairpin-forming RNA. Non-limiting examples of hairpin-forming RNA include short hairpin RNA (shRNA), microRNA (miRNA) and artificial microRNA (AmiRNA). In some embodiments, nucleic acids are provided herein that contain or encode the target recognition and binding sequences (e.g., a seed sequence or a sequence complementary to a target) of any one of the inhibitory RNAs (e.g., shRNA, miRNA, AmiRNA) disclosed herein.

Generally, hairpin-forming RNAs are arranged into a self-complementary "stem-loop" structure that includes a single nucleic acid encoding a stem portion having a duplex comprising a sense strand (e.g., passenger strand) connected to an antisense strand (e.g., guide strand) by a loop sequence. The passenger strand and the guide strand share complementarity. In some embodiments, the passenger strand and guide strand share 100% complementarity. In some embodiments, the passenger strand and guide strand share at least 50%, at least 60%, at least 70%, at least 80%, at least 90%, at least 95%, or at least 99% complementarity. A passenger strand and a guide strand may lack complementarity due to a base-pair mismatch. In some embodiments, the passenger strand and guide strand of a hairpin-forming RNA have at least 1, at least 2, at least 3, at least 4, at least 5, at least 6, at least 7 at least 8, at least 9, or at least 10 mismatches. Generally, the first 2-8 nucleotides of the stem (relative to the loop) are referred to as "seed" residues and play an important role in target recognition and binding. The first residue of the stem (relative to the loop) is referred to as the "anchor" residue. In some embodiments, hairpin-forming RNA have a mismatch at the anchor residue.

Hairpin-forming RNA are useful for translational repression and/or gene silencing via the RNAi pathway. Due to having a common secondary structure, hairpin-forming RNA share the characteristic of being processed by the proteins Drosha and Dicer prior to being loaded into the RNA-induced silencing complex (RISC). Duplex length amongst hairpin-forming RNA can vary. In some embodiments, a duplex is between about 19 nucleotides and about 200 nucleotides in length. In some embodiments, a duplex is between about between about 14 nucleotides to about 35 nucleotides in length. In some embodiments, a duplex is between about 19 and 150 nucleotides in length. In some embodiments, hairpin-forming RNA has a duplex region that is 19, 20, 21, 22, 23, 24, 25, 26, 27, 28, 29, 30, 31, 32, or 33 nucleotides in length. In some embodiments, a duplex is between about 19 nucleotides and 33 nucleotides in length. In some embodiments, a duplex is between about 40 nucleotides and 100 nucleotides in length. In some embodiments, a duplex is between about 60 and about 80 nucleotides in length.

In some embodiments, the hairpin-forming RNA is a microRNA (miRNA), or artificial microRNA (AmiRNA). A microRNA (miRNA) is a small non-coding RNA found in plants and animals and functions in transcriptional and post-translational regulation of gene expression. An artificial microRNA (AmiRNA) is derived by modifying native miRNA to replace natural targeting regions of pre-mRNA with a targeting region of interest. For example, a naturally occurring, expressed miRNA can be used as a scaffold or backbone (e.g., a pri-miRNA scaffold), with the stem sequence replaced by that of an miRNA targeting a gene of interest. An artificial precursor microRNA (pre-amiRNA) is normally processed such that one single stable small RNA is preferentially generated. In some embodiments, scAAV vectors and scAAVs described herein comprise a nucleic acid encoding an AmiRNA. In some embodiments, the pri-miRNA scaffold of the AmiRNA is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

The following non-limiting list of miRNA genes, and their homologues, which are also useful in certain embodiments of the vectors provided herein: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsamiR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-548l, hsa-miR-548m, hsa-miR-548n, hsamiR-548o, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*. In some embodiments, the above miRNAs may be encoded for in a vector provided herein (e.g., in a hairpin nucleic acid that replaces a mutant ITR). In some embodiments, sequences of the foregoing miRNAs may be useful as scaffolds or as targeting regions (e.g., seed regions of AmiRNA).

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

In some embodiments, at least one inhibitory nucleic acid is encoded by a sequence comprising at least 6 (e.g., 6, 7, 8, 9, 10, 11, 12, 13, 14, 15, 16, 17, 18, 19, 20, 21, or more) contiguous nucleotides as set forth in SEQ ID NOs: 1-6. In some embodiments, at least one inhibitory nucleic acid binds a target sequence comprising at least 6 (e.g., 6, 7, 8, 9, 10, 11, 12, 13, 14, 15, 16, 17, 18, 19, 20, 21, or more) contiguous nucleotides as set forth in SEQ ID NOs: 10-15. In some embodiments, at least one inhibitory nucleic acid is encoded by a sequence comprising at least 6 (e.g., 6, 7, 8, 9, 10, 11, 12, 13, 14, 15, 16, 17, 18, 19, 20, 21, or more) contiguous nucleotides as set forth in SEQ ID NOs: 16-21. In some embodiments, at least one inhibitory nucleic acid is encoded by a sequence comprising at least 6 (e.g., 6, 7, 8, 9, 10, 11, 12, 13, 14, 15, 16, 17, 18, 19, 20, 21, or more) contiguous nucleotides as set forth in SEQ ID NOs: 16-21, wherein the thymine nucleobases are replaced with uracil nucleobases.

In some embodiments, an inhibitory nucleic acid as described by the disclosure comprises a sequence in which thymine nucleobases have been replaced with uracil nucleobases. In some embodiments, an inhibitory nucleic acid comprises a sequence in which every thymine nucleobases has been replaced with a uracil nucleobase. In some embodiments, an inhibitory nucleic acid comprises a sequence in which 1, 2, 3, 4, 5, 6, 7, 8, 9, 10, 11, 12, 13, 14, 15, or more thymine nucleobases have been replaced with uracil nucleobases.

In some embodiments, an inhibitory nucleic acid comprises one or more mismatches with a target sequence (e.g., a sequence set forth in any one of SEQ ID NOs: 10-15). In some embodiments, an inhibitory nucleic acid has 1, 2, 3, 4, 5, 6, 7, 8, 9, or 10 mismatches relative to a target sequence, for example a SPTLC1 target sequence (e.g., any one of SEQ ID NOs: 10-15). In some embodiments, an inhibitory nucleic acid has more than 10 mismatches relative to a target sequence (e.g., a SPTLC1 target sequence). In some embodiments, an inhibitory nucleic acid does not comprise any mismatches with a target sequence (e.g., a sequence set forth in any one of SEQ ID NOs: 10-15). In some embodiments, an inhibitory nucleic acid is partially complementary to a target sequence (e.g., a sequence set forth in any one of SEQ ID NOs: 10-15). In some embodiments, an inhibitory nucleic acid is wholly complementary to a target sequence (e.g., a sequence set forth in any one of SEQ ID NOs: 10-15).

Isolated Nucleic Acids

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulated by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulated by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid further comprises a region (e.g., a second region, a third region, a fourth region, etc.) comprising a second AAV ITR.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the disclosure. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein.

A region comprising a transgene (e.g., comprising a fusion protein, etc.) may be positioned at any suitable location of the isolated nucleic acid that will enable expression of the at least one inhibitory nucleic acid, the selectable marker protein, or reporter protein.

It should be appreciated that in cases where a transgene encodes more than one polypeptide, each polypeptide may be positioned in any suitable location within the transgene. For example, a nucleic acid encoding a first polypeptide may be positioned in an intron of the transgene and a nucleic acid sequence encoding a second polypeptide may be positioned in another untranslated region (e.g., between the last codon of a protein coding sequence and the first base of the poly-A signal of the transgene).

A "promoter" refers to a DNA sequence recognized by the synthetic machinery of the cell, or introduced synthetic machinery, required to initiate the specific transcription of a gene. The phrases "operatively linked," "operatively positioned," "under control" or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the Y AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931.; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an RNA pol II promoter. In some embodiments, a promoter is an RNA pol III promoter, such as U6 or H1. In some embodiments, a promoter is an RNA pol II promoter. In some embodiments, a promoter is a chicken β-actin (CBA) promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc..) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (α-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, a transgene which encodes at least one inhibitory nucleic acid is operably linked to a promoter. In some embodiments, a transgene which encodes a selectable marker or reporter protein is operably linked to a promoter. In some embodiments, the transgene encoding at least one inhibitory nucleic acid is and the transgene which encodes a selectable marker or reporter protein are operably linked to the same promoter. In some embodiments, the transgene encoding at least one inhibitory nucleic acid is and the transgene which encodes a selectable marker or reporter protein are operably linked to different promoters. In some embodiments, the promoter is a constitutive promoter. In some embodiments, the promoter is an inducible promoter. In some embodiments, the promoter is a tissue-specific promoter. In some embodiments, the tissue-specific promoter is a neuron-specific promoter, or a central nervous system (CNS)-specific promoter. In some embodiments, the tissue-specific promoter is a synapsin promoter, a SOD1 promoter, a Chat promoter, a GFAP promoter, a calcium/calmodulin-dependent protein kinase II promoter, a tubulin alpha I promoter, a neuron-specific enolase promoter, or a platelet-derived growth factor beta chain promoter.

Aspects of the disclosure relate to an isolated nucleic acid comprising more than one promoter (e.g., 2, 3, 4, 5, or more promoters). For example, in the context of a construct having a transgene comprising a first region (e.g., an inhibitory nucleic acid) and an second region (e.g., a selectable marker protein, reporter protein, therapeutic protein, etc.) it may be desirable to drive expression of the first protein coding region using a first promoter sequence (e.g., a first promoter sequence operably linked to the first region), and to drive expression of the second region with a second promoter sequence (e.g., a second promoter sequence operably linked to the second region). Generally, the first promoter sequence and the second promoter sequence can be the same promoter sequence or different promoter sequences. In some embodiments, the first promoter sequence (e.g., the promoter driving expression of the first region) is a RNA polymerase III (pol III) promoter sequence. Non-limiting examples of pol III promoter sequences include U6 and H1 promoter sequences. In some embodiments, the second promoter sequence (e.g., the promoter sequence driving expression of the second region) is a RNA polymerase II (pol II) promoter sequence. Non-limiting examples of pol II promoter sequences include T7, T3, SP6, RSV, and cytomegalovirus promoter sequences. In some embodiments, a pol III promoter sequence drives expression of the first region. In some embodiments, a pol II promoter sequence drives expression of the second region.

Recombinant Adeno-Associated Viruses (rAAVs)

In some aspects, the disclosure provides isolated adeno-associated viruses (AAVs). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV1, AAV2, AAV3, AAV4, AAV5, AAV6, AAV7, AAV8, AAVrh8, AAV9, AAV10, AAVrh10, and AAV.PHP.B. In some embodiments, an AAV capsid protein is of a serotype derived from a non-human primate, for example AAVrh8 serotype. In some embodiments, an AAV capsid protein is of a serotype derived for broad and efficient CNS transduction, for example AAV.PHP.B. In some embodiments, the capsid protein is of AAV serotype 9.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a transgene (e.g., a DNA binding domain fused to a transcriptional regulator domain). In some embodiments, the host cell is a mammalian cell, a yeast cell, a bacterial cell, an insect cell, a plant cell, or a fungal cell.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an AAV vector (comprising a transgene flanked by ITR elements) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpes virus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. In some embodiments, a host cell is a neuron. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. In some embodiments, a vector is a viral vector, such as an rAAV vector, a lentiviral vector, an adenoviral vector, a retroviral vector, etc. Thus, the term includes cloning and expression vehicles, as well as viral vectors. In some embodiments, useful vectors are contemplated to be those vectors in which the nucleic acid segment to be transcribed is positioned under the transcriptional control of a promoter.

A "promoter" refers to a DNA sequence recognized by the synthetic machinery of the cell, or introduced synthetic machinery, required to initiate the specific transcription of a gene. The phrases "operatively linked", "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product from a transcribed gene. The foregoing methods for packaging recombinant vectors in desired AAV capsids to produce the rAAVs of the disclosure are not meant to be limiting and other suitable methods will be apparent to the skilled artisan.

Methods for Regulating Target Gene Expression

Methods for regulating target gene (e.g., SPTLC1) expression in a cell or subject are provided by the disclosure. The methods typically involve administering to a cell or a subject an isolated nucleic acid or rAAV comprising a transgene which encodes at least one inhibitory nucleic acid that targets a gene encoding an SPT protein (e.g., SPTLC1). In some embodiments, the isolated nucleic acid or rAAV further comprises a transgene encoding a therapeutic protein, a selectable marker protein, or a reporter protein. In some embodiments, an inhibitory nucleic acid is an amiRNA, an shRNA, an siRNA, microRNA, or an antisense oligonucleotide (ASO).

In some aspects, the disclosure provides methods of modulating (e.g., increasing, decreasing, etc.) expression of a target gene in a cell. In some embodiments, the modulating is decreasing expression of a target gene (e.g., SPTCL1) in a cell. In some embodiments, a cell is a mammalian cell, such as a human cell, non-human primate cell, cat cell, mouse cell, dog cell, rat cell, hamster cell, etc. In some embodiments, a cell is a neuron. In some embodiments, the neuron is a sensory neuron. Examples of sensory neurons include but are not limited to olfactory neurons, photoreceptor cells, auditory neurons, thermoreceptor neurons, and mechanoreceptor neurons (e.g., nociceptor neurons, proprioceptor neurons, etc.). In some embodiments, a cell is in a subject (e.g., in vivo).

Administering an isolated nucleic acid or an rAAV encoding a transgene as described by the disclosure to a cell or subject, in some embodiments, results in decreased expression of a target gene (e.g., SPTLC1). Thus, in some embodiments, compositions and methods described by the disclosure are useful for treating conditions resulting from dysfunction of SPT proteins and/or aberrant (e.g., increased or decreased, relative to a normal subject) expression of SPT proteins or SPT protein subunits (e.g., SPTLC1). In some embodiments, dysfunction of SPT proteins or aberrant (e.g., increased or decreased, relative to a normal subject) expression of SPT proteins or SPT protein subunits is caused by one or more missense mutations of a target gene. In some embodiments, one or more mutations of the SPTLC1 gene results in hereditary sensory and autonomic neuropathy 1 (HSAN1).

Typically, a mutation is a missense mutation, non-sense mutation, or frameshift mutation. In some embodiments, a mutation (e.g., results in a truncated SPT protein subunit).

As used herein, "missense mutations" refers to a genetic condition wherein the nucleotide sequence at least one copy of a gene (e.g., SPTCL1) is altered with respect to a wild-type gene sequence. As used herein, wild-type refers to the sequence of a gene (e.g. SPTCL1) which prevails among subjects in natural conditions. In some embodiments, a subject has missense mutations associated with HSAN1, wherein at least one copy of the SPTCL1 gene is mutated, resulting in increased SPTCL1 activity. The majority of HSAN1 patients carry SPTCL1 mutations which are translated into mutated proteins; other SPTCL1 mutations associated with HSAN1 include missense and splice-site mutations. HSAN1 (OMIM entry #164200), is a rare, autosomal dominant neuropathy which typically manifests in the first two decades of life. HSAN1 is characterized by tingling, weakness, and reduced sensitivity to sensations in the lower extremities. In severe cases, the symptoms can spread to the arms and abdomen. The only treatment currently available for HSAN1 patients alleviates the symptoms, but does not treat the cause of HSAN1.

Numerous missense mutations in SPTLC1 are associated with HSAN1. In some embodiments, the missense mutation is C133W, which is associated with increased production of sphingolipids from SPT. In some embodiments, the missense mutation is C133Y, V144D, S331F, or A352V, all of which are associated with decreased production of sphingolipids from SPT. Additional mutations of SPTLC1 are described, for example by Bode et al. Hum Mol Genet. 2016 Mar. 1; 25(5):853-65.

In some embodiments, the subject has or is suspected of having mutations in SPTCL1 that result in HSAN1. A subject that "has or is suspected of having HSAN1" refers to a subject characterized by 1) one or more signs or symptoms of HSAN1, for example tingling, weakness, reduced ability to sense pain in the hands or feet, reduced ability to sense hot or cold in the hands or feet, sensorineural hearing loss, etc., and/or 2) one or more mutations in a gene encoding a SPT protein subunit (e.g., SPTLC1) that results in dysfunction of the SPT protein, and/or a deletion (e.g., a chromosomal deletion) of a gene encoding a SPT protein.

Aspects of the disclosure relate to a subject or cell that is characterized by aberrant (e.g., increased or decreased, relative to a healthy, normal cell or subject) expression of a gene encoding an SPT protein. In some embodiments, the expression of a target gene (e.g., SPTCL1) in a normal cell or subject is sufficient such that cell or subject has wild-type expression of a target gene (e.g., SPTCL1). In some embodiments, "decreased" expression or activity of a transgene is measured relative to expression or activity of that transgene in a cell or subject who has not been administered one or more isolated nucleic acids, rAAVs, or compositions as described herein. In some embodiments, "decreased" expression or activity of a transgene is measured relative to expression or activity of that transgene in the subject after the subject has been administered (e.g., gene expression is measured pre- and post-administration of) one or more isolated nucleic acids, rAAVs, or compositions as described herein. Methods of measuring gene expression or protein levels are known in the art and include, for example, quantitative PCR (qPCR), Western Blot, mass spectrometry (MS) assays, etc.

In some embodiments, administration of an isolated nucleic acid, rAAV, or composition as described by the disclosure results in a reduction of SPTCL1 expression and/or activity in a subject between 2-fold and 100-fold (e.g., 2-fold, 5-fold, 10-fold, 50-fold, 100-fold, etc.) relative to the SPTCL1 expression and/or activity of a subject who has not been administered one or more compositions described by the disclosure.

Modes of Administration

The isolated nucleic acids, rAAVs, and compositions of the disclosure may be delivered to a subject in compositions according to any appropriate methods known in the art. For example, an rAAV, preferably suspended in a physiologically compatible carrier (e.g., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), thalamus, spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000). In some embodiments, an rAAV as described in the disclosure are administered by intravenous injection. In some embodiments, rAAVs are administered by intracerebral injection. In some embodiments, rAAVs are administered by intrathecal injection. In some embodiments, rAAVs are administered by intrastriatal injection. In some embodiments, rAAVs are delivered by intracranial injection. In some embodiments, rAAVs are delivered by cisterna magna injection. In some embodiments, the rAAV are delivered by cerebral lateral ventricle injection.

Aspects of the instant disclosure relate to compositions comprising a recombinant AAV comprising a capsid protein and a nucleic acid encoding a transgene, wherein the transgene comprises a nucleic acid sequence encoding one or more proteins. In some embodiments, the nucleic acid further comprises AAV ITRs. In some embodiments, a composition further comprises a pharmaceutically acceptable carrier.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, parachlorophenol, and poloxamers (non-ionic surfactants) such as Pluronic® F-68. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is administered to the subject during a pre-symptomatic stage of HSAN1. In some embodiments, a subject is administered an rAAV or composition after exhibiting one or more signs or symptoms of HSAN1.

In some embodiments, rAAV compositions are formulated to reduce aggregation of AAV particles in the composition, particularly where high rAAV concentrations are present (e.g., ~$10^{13}$ GC/mL or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for constructing an AAV vector as described herein. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1: Screening of microRNAs Targeting SPTLC1 In Vitro

Figure 1B:
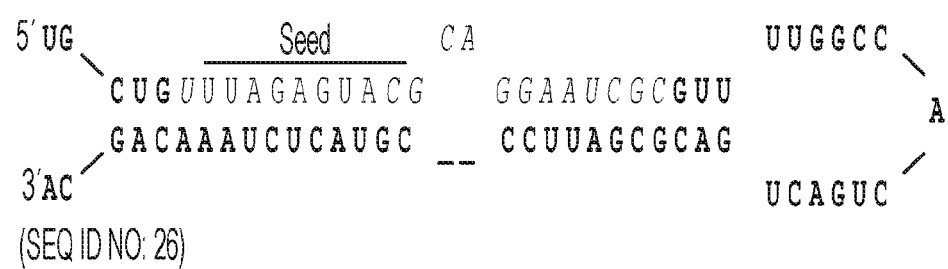
Figure 1C:
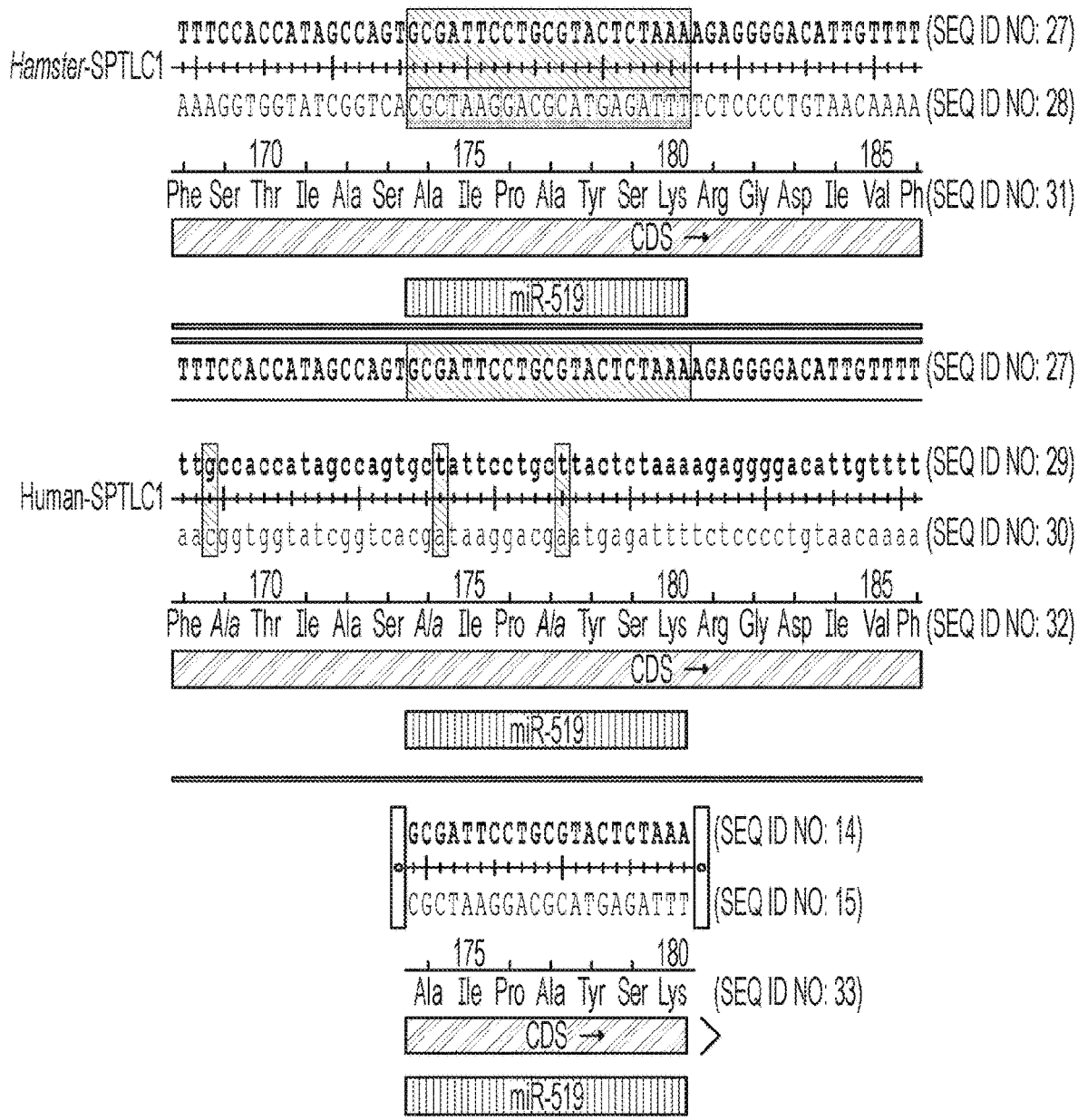

AAV Plasmid Design microRNA sequences were designed to be complementary to human, hamster, or both human and hamster SPTLC1. These microRNAs were incorporated into an AAV plasmid which comprises ITRs flanking a transgene encoding a microRNA which is operably linked to a promoter, a CMV enhancer/chicken β-actin (CB) promoter operably linked to a transgene encoding GFP, and a poly A signal (FIG. 1A). MicroRNAs form a hairpin when expressed, which comprise a seed sequence for binding complementary mRNA (FIG. 1B). The complementarity of one microRNA (miR-519) to both human and hamster SPTLC1 is shown in (FIG. 1C).

HEK293T human or CHO hamster cells were transfected with 1 µg of plasmid DNA and jetPRIME® reagent (Polypus Transfection, Illkirch, France). Total RNA was extracted from the cells 48 hours after transfection and complementary DNA (cDNA) was generated from the RNA by reverse transcription polymerase chain reaction (RT-PCR). The amount of cDNA was quantified using digital PCR. H1-amiRC9, a microRNA which targets the C9orf72 gene involved in ALS, was used as a microRNA control. CB-GFP was used as a GFP control, along with a non-transfected control. All samples were normalized to the endogenous gene HPRT. Three independent biological replicates, each comprising three technical replicates were performed. Error bars are one standard deviation above and below the mean gene expression for each condition.

Figure 2A:
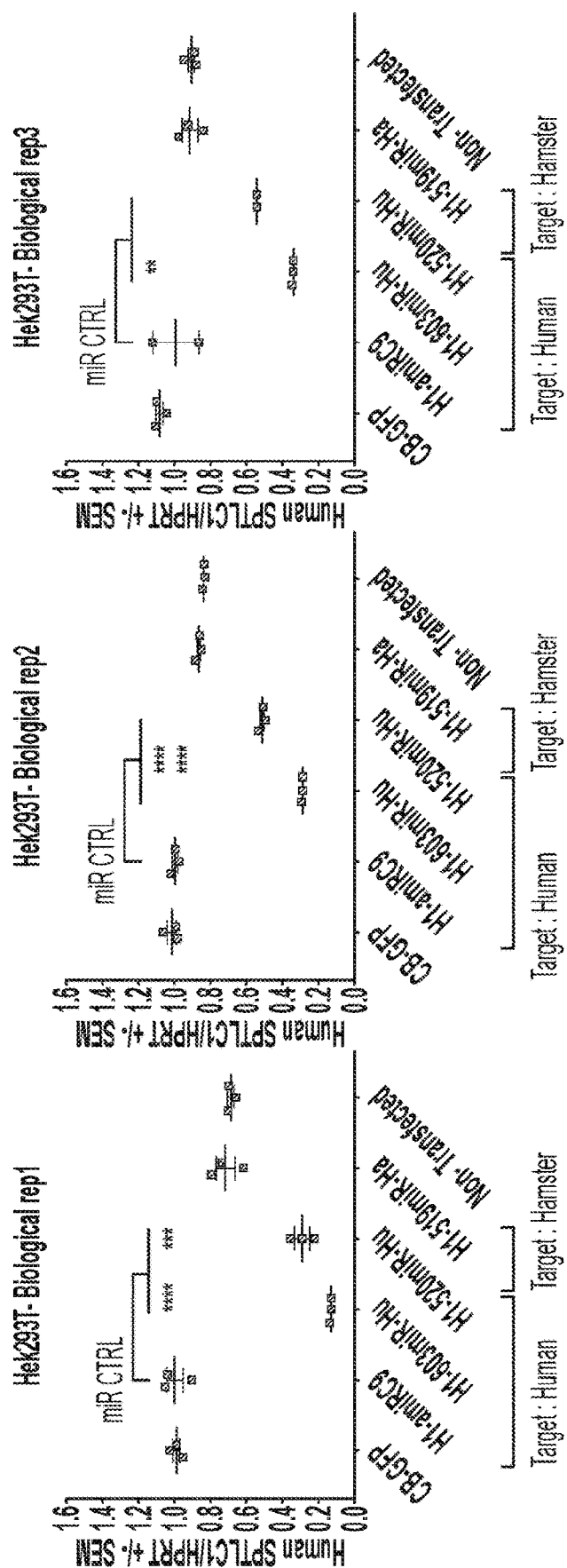
FIGS. 2A-2B are show SPTLC1 mRNA expression by digital PCR in vitro.

Expression of AAV vectors encoding 603miR and 520miR complementary to human SPTLC1 significantly reduced gene expression compared to control (FIG. 2A). This reduction of human SPTLC1 required microRNAs which were complementary to human and not hamster SPTLC1 (FIG. 2A).

Figure 2B:
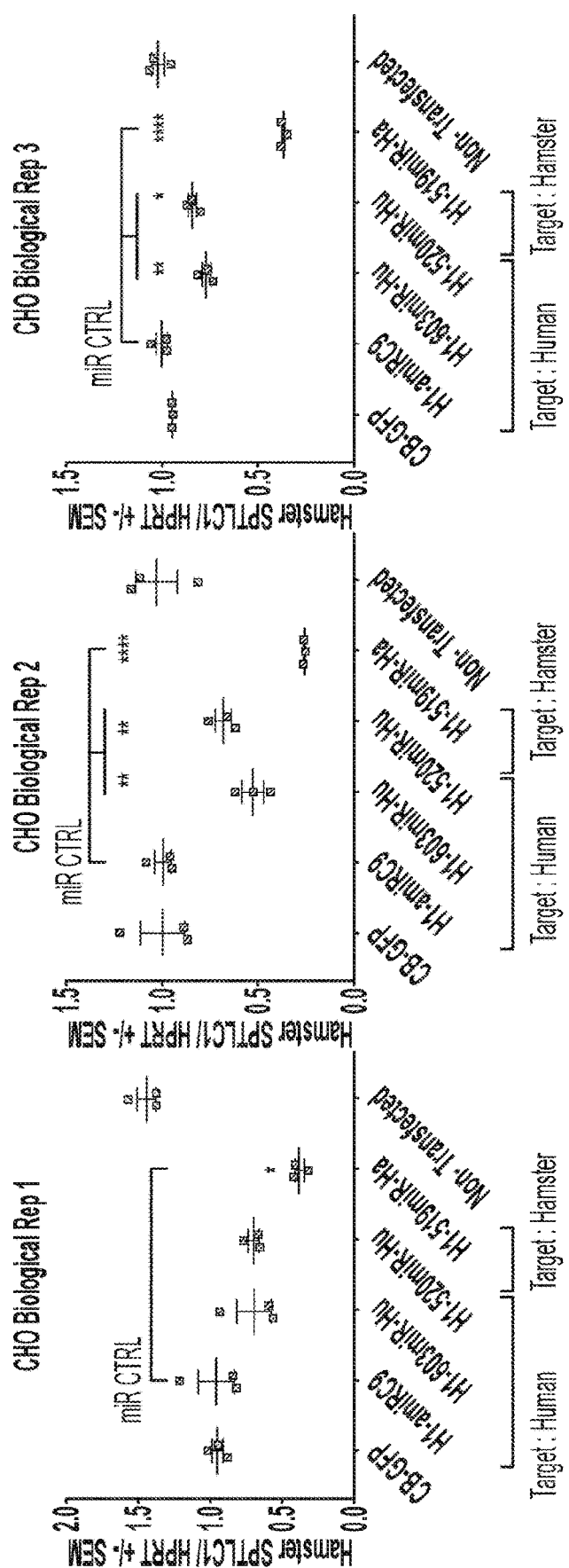

Expression of an AAV vector encoding 519miR complementary to hamster SPTLC1 significantly reduced gene expression compared to control (FIG. 2B). This reduction of hamster SPTLC1 required microRNA which was complementary to hamster, but not human SPTLC1 (FIG. 2B).

Example 2

An AAV vector encoding any one of 603miR (comprising nucleic acid sequences comprising SEQ ID NOs: 18 and 19), 520miR (comprising nucleic acid sequences comprising SEQ ID NOs: 16 and 17), or 519miR (comprising nucleic acid sequences comprising SEQ ID NOs: 20 and 21) is administered to a human patient having hereditary sensory and autonomic neuropathy 1 (HSAN1). Administration of a single dose of AAV vector is performed by intramuscular injection or by administration into the bloodstream of the patient. Following administration of the AAV vector, the expression of SPTLC1 in disease-relevant cells (e.g., dorsal root ganglion and motor neurons) is determined using RNA-SEQ technology. Assessment of the relative decrease in SPTLC1 expression resulting from the inhibitory nucleic acid(s) encoded by the AAV vector can be further determined by comparing the SPTLC1 expression level to a baseline measurement or a control.

```
SEQUENCES
In the sequences provided herein, the T nucleobases can be replaced
with U nucleobases. In some embodiments, every T nucleobase provided
in the sequences provided herein are replaced with U nucleobases. In
some embodiments, 1, 2, 3, 4, 5, 6, 7, 8, 9, 10, or more T nucleo-
bases provided in the sequences provided herein are replaced with U
nucleobases.
miR-520 Binding Sequence (Top Strand)
                                                          >SEQ ID NO: 1
TTTAGAGTAAGCAGGAATAGC miR-520 Binding Sequence (Bottom Strand)
                                                          >SEQ ID NO: 2
AAACGCTATTCCTGCTTACTC
```

-continued

```
miR-603 Binding Sequence (Top Strand)
                                                    >SEQ ID NO: 3
AACTTAATGTCACTACGGGAT miR-603 Binding Sequence (Bottom Strand)
                                                    >SEQ ID NO: 4
AAACATCCCGTAGTGACATTA miR-519 Binding Sequence (Top Strand)
                                                    >SEQ ID NO: 5
TTTAGAGTACGCAGGAATCGC miR-519 Binding Sequence (Bottom Strand)
                                                    >SEQ ID NO: 6
AAACGCGATTCCTGCGTACTC miR-520 Seed Sequence
                                                    >SEQ ID NO: 7
UUAGAGUA miR-603 Seed Sequence
                                                    >SEQ ID NO: 8
ACUUAAUG miR-519 Seed Sequence
                                                    >SEQ ID NO: 9
UUAGAGUA miR-520 Target Sequence (Top Strand)
                                                    >SEQ ID NO: 10
GCTATTCCTGCTTACTCTAAA miR-520 Target Sequence (Bottom Strand)
                                                    >SEQ ID NO: 11
TTTAGAGTAAGCAGGAATAGC miR-603 Target Sequence (Top Strand)
                                                    >SEQ ID NO: 12
ATCCCGTAGTGACATTAAGTT miR-603 Target Sequence (Bottom Strand)
                                                    >SEQ ID NO: 13
AACTTAATGTCACTACGGGAT miR-519 Target Sequence (Top Strand)
                                                    >SEQ ID NO: 14
GCGATTCCTGCGTACTCTAAA miR-519 Target Sequence (Bottom Strand)
                                                    >SEQ ID NO: 15
CGCTAAGGACGCATGAGATTT miR-520 (Top Strand)
                                                    >SEQ ID NO: 16
TGCTGTTTAGAGTAAGCAGGAATAGCGTTTTGGCCACTGACTGACGCTATTCCCTTA
CTCTAAA miR-520 (Bottom Strand)
                                                    >SEQ ID NO: 17
CCTGTTTAGAGTAAGGGAATAGCGTCAGTCAGTGGCCAAAACGCTATTCCTGCTTAC
TCTAAC miR-603 (Top Strand)
                                                    >SEQ ID NO: 18
TGCTGAACTTAATGTCACTACGGGATGTTTTGGCCACTGACTGACATCCCGTAGACA
TTAAGTT miR-603 (Bottom Strand)
                                                    >SEQ ID NO: 19
CCTGAACTTAATGTCTACGGGATGTCAGTCAGTGGCCAAAACATCCCGTAGTGACA
TTAAGTTC
``` miR-519 (Top Strand)
>SEQ ID NO: 20
TGCTGTTTAGAGTACGCAGGAATCGCGTTTTGGCCACTGACTGACGCGATTCCCGTA
CTCTAAA miR-519 (Bottom Strand)
>SEQ ID NO: 21
CCTGTTTAGAGTACGGGAATCGCGTCAGTCAGTGGCCAAAACGCGATTCCTGCGTA
CTCTAAAC human SPTCL1 nucleotide sequence
>SEQ ID NO: 22
CGCTCCGCCGCCCCGCCCTCTGCGGAGGTGATAACGACACTGAGCAGCGACGCGCA
CTTTTGGGACGCGCTTGTGACCCGCCTTCCGGAAGGAAGCGGCTAACTATGGCGAC
CGCCACGGAGCAGTGGGTTCTGGTGGAGATGGTACAGGCGCTTTACGAGGCTCCTG
CTTACCATCTTATTTTGGAAGGGATTCTGATCCTCTGGATAATCAGACTTCTTTTCTC
TAAGACTTACAAATTACAAGAACGATCTGATCTTACAGTCAAGGAAAAAGAAGAAC
TGATTGAAGAGTGGCAACCAGAACCTCTTGTTCCTCCTGTCCCAAAAGACCATCCTG
CTCTCAACTACAACATCGTTTCAGGCCCTCCAAGCCACAAAACTGTGGTGAATGGA
AAAGAATGTATAAACTTCGCCTCATTTAATTTTCTTGGATTGTTGGATAACCCTAGG
GTTAAGGCAGCAGCTTTAGCATCTCTAAAGAAGTATGGCGTGGGGACTTGTGGACC
CAGAGGATTTTATGGCACATTTGATGTTCATTTGGATTTGGAAGACCGCCTGGCAAA
ATTTATGAAGACAGAAGAAGCCATTATATACTCATATGGATTTGCCACCATAGCCA
GTGCTATTCCTGCTTACTCTAAAAGAGGGGACATTGTTTTTGTAGATAGAGCTGCCT
GCTTTGCTATTCAGAAAGGATTACAGGCATCCCGTAGTGACATTAAGTTATTTAAGC
ATAATGACATGGCTGACCTCGAGCGACTACTAAAAGAACAAGAGATCGAAGATCA
AAAGAATCCTCGCAAGGCTCGTGTAACTCGGCGTTTCATTGTAGTAGAAGGATTGT
ATATGAATACTGGAACTATTTGTCCTCTTCCAGAATTGGTTAAGTTAAAATACAAAT
ACAAAGCAAGAATCTTCCTGGAGGAAAGCCTTTCATTTGGAGTCCTAGGAGAGCAT
GGCCGAGGAGTCACTGAACACTATGGAATCAATATTGATGATATTGATCTTATCAGT
GCCAACATGGAGAATGCACTTGCTTCTATTGGAGGTTTCTGCTGTGGCAGGTCTTTT
GTAATTGACCATCAGCGACTTTCCGGCCAGGGATACTGCTTTTCAGCTTCGTTACCT
CCCCTGTTAGCTGCTGCAGCAATTGAGGCCCTCAACATCATGGAAGAGAATCCAGG
TATTTTTGCAGTGTTGAAGGAAAAGTGCGGACAAATTCATAAAGCTTTACAAGGCA
TTTCTGGATTAAAAGTGGTGGGGAGTCCCTTTCTCCAGCCTTTCACCTACAACTGG
AAGAGAGCACTGGGTCTCGCGAGCAAGATGTCAGACTGCTTCAGGAAATTGTAGAT
CAATGCATGAACAGAAGTATTGCATTAACTCAGGCGCGCTACTTGGAGAAAGAAGA
GAAGTGTCTCCCTCCTCCCAGAGGAAGAACTGGAGAGAGCTGCGTCCACCATCAAG
GAGGTAGCCCAGGCCGTCCTGCTCTAGGCAGAGTCCCGGGACCATGGCCTCCTGCC
ACACAACACGCAGAGAGGACTCAAGACTCCCGCTGGCCATGGAGTGGCCTGAAAG
AGAGCAAGAACATGTGGATCTTTGATAGGATTGTTACCAAATGGTGTCAGTATGGA
CCAATTGTGTGACCATGAGAAGGATGCTTATTTTTTTAAAAAGAAAACACATCTAA
AAGCCCAGGAACTGATTTTTTTAAGAGGAAAACTAATGACAGTGTATAACTGATGT
TTAAATTGTGCATTTAGTACTATTTAAATGTTTTCTTATACTAGTATTTTATATTCTTT
TGTTGTCGTTTAAAACTGGAGCTTCAGTGTCTCTTCCCTCCCTCTAATAGTAATGGTT -continued

```
CAGTAAGCACTCCTTAACTCCTTAGTATTTCATAGAAAAATGACTGCAACATTAAAG

CTAAGAGGAACACTTCAACATATGTGGTACAAATTTATATTGAAGATCTAAATAAA

CCACGTATTTTCCAGTCTTCGTTGTGTGAAGCTAAATGGTGGCTAAAAGGAACACTT

TTTGTGTGATTATTATAAACTTTGCATTGTATTTGAATCTTAGAACTTTTGTACACAC

TAAATATTGATGTCACACCATTTCTAATCTGAGCATCCTTAGCCAGAGAATATTCAT

TATACTTCCTAAGTGAGCAATAATTTAAATCAGAAGCTATTTTATTTTAATGTAATT

AACCTTTCTTTACATTTCTTATGTGTTCACCTCTAATCTGTTTTAGGAAGAGAGTTGG

TTATTATGTTGATCCCATAATATAAATCATATCCTTTATATTTTAGAATATCTCAAAT

GTATTCCTTTTTTGTATGGTGGGTTTGCCTAGGGACGTGTAACTACAGGCTTTTACTA

AGCCAAGGAAAAAGAGAATTTTTCTTTTCATCTTACAAATTCCAGATATCTACAAAA

GATGTGAAAGCACTAAAAATACCATTTTTAAGCAGTACTTTACCTGTTTTTTCTTTA

GCAAACCAGGTTATGTGGTGTAAAGGTTTGTTATACGTGCCACAATATAGCATATA

AATATTATGCCATCATTCCTTCTCTTGTTAAAGGTAGAAGAATAAAATTGTGATTTT

TATAACCTGTGCTTATTACTCAAATGGTCTTCAACATCTTTTTAAACAACACATACTT

TTTGAATGTTCAGTTTCTATTTTGCTTGAGGTATTTTGTACATATGTGCCTTGTGATT

GCTGCTGCTTTAAAGGATAAAGTACTCTTTGGGGGATGAGTCTGGTTTGTTTTGTTTT

ATTTTTTAATGAAATAAACCTATATTCCTGATTATTAGTCTATTAAAAAAAA
``` mouse SPTCL1 nucleotide sequence

>SEQ ID NO: 23

```
GGCTGCCTGACCATGGCGACAGTGGCGGAGCAGTGGGTGCTGGTGGAGATGGTGCA

GGCGCTGTACGAGGCTCCAGCATACCATCTTATTTTGGAAGGAATCCTAATACTTTG

GATAATCAGACTCGTTTTCTCTAAAACTTACAAGTTGCAGGAGCGTTCTGATCTTAC

AGCCAAGGAAAAGGAAGAACTGATTGAAGAGTGGCAGCCAGAGCCCCTCGTCCCT

CCAGTCTCCAAGAACCACCCTGCTCTCAACTACAACATCGTGTCCGGCCCTCCAACC

CACAACATCGTGGTGAATGGAAAAGAGTGTGTCAACTTTGCCTCCTTTAACTTCCTT

GGGCTGCTGGCCAACCCTCGAGTTAAGGCCACAGCTTTTTCATCTTTAAAGAAGTAC

GGAGTGGGTACCTGTGGTCCTCGAGGGTTCTATGGCACATTTGATGTCCATCTGGAT

TTAGAAGAGCGCCTGGCAAAGTTTATGAAGACCGAAGAAGCCATCATTTACTCGTA

TGGCTTCTCCACCATAGCCAGTGCCATTCCTGCGTACTCTAAGAGAGGGGACATCAT

CTTTGTGGACAGTGCGGCCTGCTTTGCTATCCAGAAAGGATTACAGGCATCAAGAA

GTGACATTAAGTTATTTAAGCATAATGATGTGGCTGACCTGGAGCGACTGCTAAAA

GAACAAGAGATTGAAGATCAAAAGAATCCTCGCAAGGCCCGTGTGACTCGGCGGTT

CATCGTGGTGGAGGGCTTGTACATGAACACTGGAACCATCGTCCCCTTCCAGAACT

GGTTAAATTAAAATATAAATATAAAGCAAGAATATTCCTGGAGGAGAGCCTGTCCT

TTGGAGTCCTTGGGGAGCACGGGCGAGGAGTCACCGAGCACTATGGGATCAGTATT

GATGATATTGACCTTATCAGTGCTAACATGGAGAATGCACTCGCTTCTGTCGGGGGC

TTCTGCTGTGGCCGCTCCTTCGTGGTTGACCATCAGCGGCTCTCCGGTCAAGGATAC

TGCTTTTCTGCTTCGTTACCTCCCCTGCTAGCTGCTGCTGCCATTGAGGCCCTCAACA

TCATGGAAGAGAATCCAGATATTTTTGCAGTTTTAAAGAAAAAATGCCAGAACATC

CATAAGTCTCTACAAGGTGTTTCGGGTTTAAAAGTGGTGGGAGAGTCCCTTTCTCCG

GCGCTTCATCTCCAGCTGGAAGAGAGCACGGGCTCTCGGGAGAAAGATGTGAAGCT

GCTTCAAGCAATCGTAGATCAGTGCATGGATAAGGGCATCGCATTGACTCAGGCAC
```

```
GGTACTTGGACAAGGAAGAGAAGTGCCTTCCTCCTCCAAGCATCAGGGTTGTGGTC

ACTGTGGAGCAGACGGAGGAAGAGCTACAGAGGGCTGCATCCACCATCAGGGAGG

CGGCCCAGGCTGTGCTGTTGTAGGCTCCTGCCCAGTGCTTCAGCCATGTCACCTGCG

GACGGAACTACTCAGAGACCTCCAGCTGCCCAGGGTGTGGCTGTGCTTGAATACAC

AGCCAGAGTGGATGGTTGTATCCAGCAGGAGCTGACTTGTAGAGGATGACAGATGA

CAGCATATCCCTGGTGTTTCTGCAGTGCCGTGTGCTCTGTCAGGATGCTTCACTGTC

ATTTGTATTCGCTTTTGTTTAAAACTGGAGCTTCCATTTTCCCTCTGTCGTCTGTGGG

AATGATTCAATAAGCACTTCTCCGTATCCATAGAAAAGGACTTTGCAGCTAAGAGG

GACTCTCCATGTATCCAGTTACTGTGGGAGACTGAGAGACTGTGTCCTCCCCTGTCC

TCAGGCAGAGCTCAGTGGTGGCTGCTATGCAGATACTCTGTGTGTGTTATAAACGTC

ATACAACATGGTGATCCTAGGACTCTATGTGCTCCAGTTACTGATACTGTCCTGTCT

AATCTGAGCTTCACTAACAGATCTTCATACCGCTTCCTAAGCAATAATCTGAATCAA

ACGTTATTTTATTTTTGTGTAATTGACTTTATATTTTTATATATTCTCTAGTCAGTTT

TGGGAAGAGGGTTATTATTCTGATCCCCAAATACAAATCATGCCCTTGGTATTTTCT

AATATGTCCAATGTCCTTTTTCATGGTGGTTTTGTCCAGGAGCATAGACCTGTGGGC

TTTTTCTAAGCTGAGAAAAATGAGACCTTTCCTCTTTCACTCTATAAATTCCAGATG

CCTCCGAAAAATAGGGATGCTCTAAACGTGATTTCCGAGCTCTACACTGGCTGCCGT

TGTCCTTAGCGAGCGTGTTGAGTGATATAAAGGCTTGTGACATGTGCCACGGATCGT

GTGCATGGAAGGCCTTCTCTTGTTGCACGGGCAGAGGAGTCAGGTCATTTAAATGTC

ATTTTCTGATGTGCGTTCATGTGAACCATGGGTCGGCATCTTCTTAAGTGATCTGTG

ACATTTTTAATGTTTCTATTTCATACGTGCCTTGTGATTGCTGCTGCTGTGAGGGTAC

ACTCCTGTCGGGGAAAAGTCTGTTTTGGTTTGGTTTTTAATGAAATAAACCTCCAAG

AGCTTACATTCCTGAAAAAAAAAAAAAA
``` human SPTCL1 amino acid sequence
                                                         >SEQ ID NO: 24
MATATEQWVLVEMVQALYEAPAYHLILEGILILWIIRLLFSKTYKLQERSDLTVKEKEE

LIEEWQPEPLVPPVPKDHPALNYNIVSGPPSHKTVVNGKECINFASFNFLGLLDNPRVKA

AALASLKKYGVGTCGPRGFYGTFDVHLDLEDRLAKFMKTEEAIIYSYGFATIASAIPAYS

KRGDIVFVDRAACFAIQKGLQASRSDIKLFKHNDMADLERLLKEQEIEDQKNPRKARVT

RRFIVVEGLYMNTGTICPLPELVKLKYKYKARIFLEESLSFGVLGEHGRGVTEHYGINID

DIDLISANMENALASIGGFCCGRSFVIDHQRLSGQGYCFSASLPPLLAAAAIEALNIMEEN

PGIFAVLKEKCGQIHKALQGISGLKVVGESLSPAFHLQLEESTGSREQDVRLLQEIVDQC

MNRSIALTQARYLEKEEKCLPPPSIRVVVTVEQTEEELERAASTIKEVAQAVLL mouse SPTLC1 amino acid sequence
                                                         >SEQ ID NO: 25
MATVAEQWVLVEMVQALYEAPAYHLILEGILILWIIRLVFSKTYKLQERSDLTAKEKEE

LIEEWQPEPLVPPVSKNHPALNYNIVSGPPTHNIVVNGKECVNFASFNFLGLLANPRVKA

TAFSSLKKYGVGTCGPRGFYGTFDVHLDLEERLAKFMKTEEAIIYSYGFSTIASAIPAYS

KRGDIIFVDSAACFAIQKGLQASRSDIKLFKHNDVADLERLLKEQEIEDQKNPRKARVTR

RFIVVEGLYMNTGTICPLPELVKLKYKYKARIFLEESLSFGVLGEHGRGVTEHYGISIDDI

DLISANMENALASVGGFCCGRSFVVDHQRLSGQGYCFSASLPPLLAAAAIEALNIMEEN

PDIFAVLKKKCQNIHKSLQGVSGLKVVGESLSPALHLQLEESTGSREKDVKLLQAIVDQ

CMDKGIALTQARYLDKEEKCLPPPSIRVVVTVEQTEEELQRAASTIREAAQAVLL

What is claimed is:

1. An isolated nucleic acid comprising a transgene encoding at least one inhibitory nucleic acid, wherein the at least one inhibitory nucleic acid comprises a nucleic acid sequence that is complementary to a nucleic acid encoding a serine palmitoyltransferase subunit, wherein the transgene is flanked by inverted terminal repeats (ITRs) derived from adeno-associated virus (AAV), wherein the at least one inhibitory nucleic acid is a microRNA (miRNA) or an artificial microRNA (amiRNA), and wherein the at least one inhibitory nucleic acid comprises:

(i) a first strand comprising SEQ ID NO: 16 and a second strand comprising SEQ ID NO: 17;

(ii) a first strand comprising SEQ ID NO: 18 and a second strand comprising SEQ ID NO: 19; or (iii) a first strand comprising SEQ ID NO: 20 and a second strand comprising SEQ ID NO: 21.

2. The isolated nucleic acid of claim 1, wherein the ITRs are AAV1 ITRs, AAV2 ITRs, AAV3 ITRs, AAV4 ITRs, AAV5 ITRs, AAV6 ITRs, AAV7 ITRs, AAV8 ITRs, AAVrh8 ITRs, AAV9 ITRs, or AAV10 ITRs.

3. An isolated host cell comprising the isolated nucleic acid of claim 1.

4. The isolated nucleic acid of claim 1, wherein the transgene further comprises a promoter.

5. The isolated nucleic acid of claim 4, wherein the promoter is a neuron-specific promoter or a central nervous system (CNS)-specific promoter.

6. The isolated nucleic acid of claim 4, wherein the promoter is a cytomegalovirus (CMV) promoter, a chicken beta-actin (CBA) promoter, a CMV/CBA promoter, a synapsin promoter, a SOD1 promoter, a Chat promoter, a GFAP promoter, a calcium/calmodulin-dependent protein kinase II promoter, a tubulin alpha I promoter, a neuron-specific enolase promoter, or a platelet-derived growth factor beta chain promoter.

7. A recombinant AAV (rAAV) comprising:
(i) an isolated nucleic acid comprising a transgene encoding an inhibitory nucleic acid, wherein the inhibitory nucleic acid comprises a nucleic acid sequence that is complementary to a nucleic acid sequence encoding a serine palmitoyltransferase subunit, wherein the transgene is flanked by inverted terminal repeats (ITRs) derived from adeno-associated virus (AAV), wherein the inhibitory nucleic acid is a microRNA (miRNA) or an artificial microRNA (amiRNA), and wherein the inhibitory nucleic acid comprises:
 a first strand comprising SEQ ID NO: 16 and a second strand comprising SEQ ID NO: 17;
 a first strand comprising SEQ ID NO: 18 and a second strand comprising SEQ ID NO: 19; or
 a first strand comprising SEQ ID NO: 20 and a second strand comprising SEQ ID NO: 21; and
(ii) at least one capsid protein.

8. The rAAV of claim 7, wherein the ITRs are AAV1 ITRs, AAV2 ITRs, AAV3 ITRs, AAV4 ITRs, AAV5 ITRs, AAV6 ITRs, AAV7 ITRs, AAV8 ITRs, AAVrh8 ITRs, AAV9 ITRs, or AAV10 ITRs.

9. The rAAV of claim 7, wherein the serotype of the at least one capsid protein is selected from the group consisting of: AAV1, AAV2, AAV3, AAV4, AAV5, AAV6, AAV7, AAV8, AAVrh8, AAV9, AAV10, AAVrh10, and AAV.PHPB.

* * * * *

SEQUENCE LISTING

<160> NUMBER OF SEQ ID NOS: 33

<210> SEQ ID NO 1
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1
tttagagtaa gcaggaatag c                                         21

<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 2
aaacgctatt cctgcttact c                                         21

<210> SEQ ID NO 3
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 3
aacttaatgt cactacggga t                                         21

<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 4
aaacatcccg tagtgacatt a                                         21

<210> SEQ ID NO 5
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 5
tttagagtac gcaggaatcg c                                         21

<210> SEQ ID NO 6
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 6
aaacgcgatt cctgcgtact c                                              21

<210> SEQ ID NO 7
<211> LENGTH: 8
<212> TYPE: RNA
<213> ORGANISM: Artificial Sequence
<220> FEATURE:
<223> OTHER INFORMATION: Synthetic Polynucleotide

<400> SEQUENCE: 7 uuagagua                                                              8

<210> SEQ ID NO 8
<211> LENGTH: 8
<212> TYPE: RNA
<213> ORGANISM: Artificial Sequence
<220> FEATURE:
<223> OTHER INFORMATION: Synthetic Polynucleotide

<400> SEQUENCE: 8 acuuaaug                                                              8

<210> SEQ ID NO 9
<211> LENGTH: 8
<212> TYPE: RNA
<213> ORGANISM: Artificial Sequence
<220> FEATURE:
<223> OTHER INFORMATION: Synthetic Polynucleotide

<400> SEQUENCE: 9 uuagagua                                                              8

<210> SEQ ID NO 10
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 10
gctattcctg cttactctaa a                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 11
tttagagtaa gcaggaatag c                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 12
atcccgtagt gacattaagt t                                              21

<210> SEQ ID NO 13

```
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 13
aacttaatgt cactacggga t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 14
gcgattcctg cgtactctaa a                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 15
cgctaaggac gcatgagatt t                                              21

<210> SEQ ID NO 16
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 16
tgctgtttag agtaagcagg aatagcgttt tggccactga ctgacgctat tcccttactc    60
taaa                                                                 64

<210> SEQ ID NO 17
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 17
cctgtttaga gtaagggaat agcgtcagtc agtggccaaa acgctattcc tgcttactct    60
aac                                                                  63

<210> SEQ ID NO 18
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 18
tgctgaactt aatgtcacta cgggatgttt tggccactga ctgacatccc gtagacatta    60
agtt                                                                 64

<210> SEQ ID NO 19
<211> LENGTH: 64
```

```
<212> TYPE: DNA
<213> ORGANISM: Artificial Sequence
<220> FEATURE:
<223> OTHER INFORMATION: Synthetic Polynucleotide

<400> SEQUENCE: 19
cctgaactta atgtctacgg gatgtcagtc agtggccaaa acatcccgta gtgacattaa    60
gttc                                                                 64

<210> SEQ ID NO 20
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 20
tgctgtttag agtacgcagg aatcgcgttt tggccactga ctgacgcgat tcccgtactc    60
taaa                                                                 64

<210> SEQ ID NO 21
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 21
cctgtttaga gtacgggaat cgcgtcagtc agtggccaaa acgcgattcc tgcgtactct    60
aaac                                                                 64

<210> SEQ ID NO 22
<211> LENGTH: 2833
<212> TYPE: DNA
<213> ORGANISM: Homo sapiens

<400> SEQUENCE: 22
cgctccgccg ccccgccctc tgcggaggtg ataacgacac tgagcagcga cgcgcacttt    60
tgggacgcgc ttgtgacccg ccttccggaa ggaagcggct aactatggcg accgccacgg   120
agcagtgggt tctggtggag atggtacagg cgctttacga ggctcctgct taccatctta   180
ttttggaagg gattctgatc ctctggataa tcagacttct tttctctaag acttacaaat   240
tacaagaacg atctgatctt acagtcaagg aaaagaaga actgattgaa gagtggcaac   300
cagaacctct tgttcctcct gtcccaaaag accatcctgc tctcaactac aacatcgttt   360
caggccctcc aagccacaaa actgtggtga tggaaaaga atgtataaac ttcgcctcat   420
ttaattttct tggattgttg gataacccta gggttaaggc agcagcttta gcatctctaa   480
agaagtatgg cgtggggact tgtggaccca gaggatttta tggcacattt gatgttcatt   540
tggatttgga agaccgcctg gcaaaattta tgaagacaga agaagccatt atatactcat   600
atggatttgc caccatagcc agtgctattc ctgcttactc taaaagaggg acattgttt   660 ttgtagatag agctgcctgc tttgctattc agaaaggatt acaggcatcc cgtagtgaca   720
ttaagttatt taagcataat gacatggctg acctcgagcg actactaaaa gaacaagaga   780
tcgaagatca aagaatcct cgcaaggctc gtgtaactcg gcgtttcatt gtagtagaag   840
gattgtatat gaatactgga actatttgtc ctcttccaga attggttaag ttaaaataca   900
aatacaaagc aagaatcttc ctggaggaaa gcctttcatt tggagtccta ggagagcatg   960
```

-continued

```
gccgaggagt cactgaacac tatggaatca atattgatga tattgatctt atcagtgcca      1020
acatggagaa tgcacttgct tctattggag gtttctgctg tggcaggtct tttgtaattg      1080
accatcagcg actttccggc cagggatact gcttttcagc ttcgttacct ccctgttag       1140 ctgctgcagc aattgaggcc ctcaacatca tggaagagaa tccaggtatt tttgcagtgt     1200
tgaaggaaaa gtgcggacaa attcataaag ctttacaagg catttctgga ttaaaagtgg     1260
tgggggagtc cctttctcca gcctttcacc tacaactgga agagagcact gggtctcgcg     1320
agcaagatgt cagactgctt caggaaattg tagatcaatg catgaacaga agtattgcat     1380
taactcaggc gcgctacttg gagaaagaag agaagtgtct ccctcctccc agaggaagaa    1440
ctggagagag ctgcgtccac catcaaggag gtagcccagg ccgtcctgct ctaggcagag     1500
tcccgggacc atggcctcct gccacacaac acgcagagag gactcaagac tcccgctggc    1560
catggagtgg cctgaaagag agcaagaaca tgtggatctt tgataggatt gttaccaaat     1620
ggtgtcagta tggaccaatt gtgtgaccat gagaaggatg cttattttt ttaaaaagaa      1680 aacacatcta aaagcccagg aactgatttt tttaagagga aaactaatga cagtgtataa    1740
ctgatgttta aattgtgcat ttagtactat ttaaatgttt tcttatacta gtattttata     1800
ttcttttgtt gtcgtttaaa actggagctt cagtgtctct tccctccctc taatagtaat     1860
ggttcagtaa gcactcctta actccttagt atttcataga aaatgactg caacattaaa     1920 gctaagagga acacttcaac atatgtggta caaatttata ttgaagatct aaataaacca    1980
cgtattttcc agtcttcgtt gtgtgaagct aaatggtggc taaaaggaac acttttgtg    2040 tgattattat aaactttgca ttgtatttga atcttagaac ttttgtacac actaaatatt     2100
gatgtcacac catttctaat ctgagcatcc ttagccagag aatattcatt atacttccta    2160
agtgagcaat aatttaaatc agaagctatt ttattttaat gtaattaacc tttcttaca   2220 tttcttatgt gttcacctct aatctgttt aggaagagag ttggttatta tgttgatccc     2280
ataatataaa tcatatcctt tatattttag aatatctcaa atgtattcct ttttgtatg     2340 gtgggtttgc ctagggacgt gtaactacag gcttttacta agccaaggaa aaagagaatt    2400
tttcttttca tcttacaaat tccagatatc tacaaaagat gtgaaagcac taaaaatacc    2460
atttttaagc agtactttac ctgttttttc tttagcaaac caggttatgt ggtgtaaagg    2520
tttgttatac gtgccacaat atagcatata aatattatgc catcattcct tctcttgtta    2580
aaggtagaag aataaaattg tgatttttat aacctgtgct tattactcaa atggtcttca    2640
acatcttttt aaacaacaca tacttttga atgttcagtt tctattttgc ttgaggtatt     2700
ttgtacatat gtgccttgtg attgctgctg ctttaaagga taaagtactc tttgggggat    2760
gagtctggtt tgttttgttt tattttttaa tgaaataaac ctatattcct gattattagt    2820
ctattaaaaa aaa                                                         2833
```

<210> SEQ ID NO 23
<211> LENGTH: 2580
<212> TYPE: DNA
<213> ORGANISM: Mus musculus

<400> SEQUENCE: 23

```
ggctgcctga ccatggcgac agtggcggag cagtgggtgc tggtggagat ggtgcaggcg      60
ctgtacgagg ctccagcata ccatcttatt ttggaaggaa tcctaatact ttggataatc     120
agactcgttt tctctaaaac ttacaagttg caggagcgtt ctgatcttac agccaaggaa    180
aaggaagaac tgattgaaga gtggcagcca gagcccctcg tccctccagt ctccaagaac    240
```

```
caccctgctc tcaactacaa catcgtgtcc ggccctccaa cccacaacat cgtggtgaat    300
ggaaaagagt gtgtcaactt tgcctccttt aacttccttg gctgctggc caaccctcga    360 gttaaggcca cagcttttc atctttaaag aagtacggag tgggtacctg tggtcctcga    420
gggttctatg gcacatttga tgtccatctg gatttagaag agcgcctggc aaagtttatg    480
aagaccgaag aagccatcat ttactcgtat ggcttctcca ccatagccag tgccattcct    540
gcgtactcta agagagggga catcatcttt gtggacagtg cggcctgctt tgctatccag    600
aaaggattac aggcatcaag aagtgacatt aagttattta agcataatga tgtggctgac    660
ctggagcgac tgctaaaaga acaagagatt gaagatcaaa agaatcctcg caaggcccgt    720
gtgactcggc ggttcatcgt ggtggagggc ttgtacatga acactggaac catctgtccc    780
cttccagaac tggttaaatt aaaatataaa tataaagcaa gaatattcct ggaggagagc    840
ctgtcctttg gagtccttgg ggagcacggg cgaggagtca ccgagcacta tgggatcagt    900
attgatgata ttgaccttat cagtgctaac atggagaatg cactcgcttc tgtcggggc    960 ttctgctgtg gccgctcctt cgtggttgac catcagcggc tctccggtca aggatactgc    1020
ttttctgctt cgttacctcc cctgctagct gctgctgcca ttgaggccct caacatcatg    1080
gaagagaatc cagatatttt tgcagtttta agaaaaaat gccagaacat ccataagtct    1140
ctacaaggtg tttcgggttt aaaagtggtg ggagagtccc tttctccggc gcttcatctc    1200
cagctggaag agagcacggg ctctcgggag aaagatgtga agctgcttca agcaatcgta    1260
gatcagtgca tggataaggg catcgcattg actcaggcac ggtacttgga caaggaagag    1320
aagtgccttc ctcctccaag catcagggtt gtggtcactg tggagcagac ggaggaagag    1380
ctacagaggg ctgcatccac catcagggag gcggcccagg ctgtgctgtt gtaggctcct    1440
gcccagtgct tcagccatgt cacctgcgga cggaactact cagagacctc cagctgccca    1500
gggtgtggct gtgcttgaat acacagccag agtggatggt tgtatccagc aggagctgac    1560
ttgtagagga tgacagatga cagcatatcc ctggtgtttc tgcagtgccg tgtgctctgt    1620
caggatgctt cactgtcatt tgtattcgct tttgtttaaa actggagctt ccatttccc    1680 tctgtcgtct gtgggaatga ttcaataagc acttctccgt atccatagaa aaggactttg    1740
cagctaagag ggactctcca tgtatccagt tactgtggga gactgagaga ctgtgtcctc    1800
ccctgtcctc aggcagagct cagtggtggc tgctatgcag atactctgtg tgtgttataa    1860
acgtcataca acatggtgat cctaggactc tatgtgctcc agttactgat actgtcctgt    1920
ctaatctgag cttcactaac agatcttcat accgcttcct aagcaataat ctgaatcaaa    1980
cgttatttta tttttgtgta attgactta tatttttat atattctcta gtcagttttg    2040
ggaagagggt tattattctg atccccaaat acaaatcatg cccttggtat ttctaatat    2100 gtccaatgtc ctttttcatg gtggttttgt ccaggagcat agacctgtgg cttttcta    2160 agctgagaaa aatgagacct ttcctctttc actctataaa ttccagatgc ctccgaaaaa    2220
tagggatgct ctaaacgtga tttccgagct ctacactggc tgccgttgtc cttagcgagc    2280
gtgttgagtg atataaaggc ttgtgacatg tgccacggat cgtgtgcatg gaaggccttc    2340
tcttgttgca cgggcagagg agtcaggtca tttaaatgtc attttctgat gtgcgttcat    2400
gtgaaccatg ggtcggcatc ttcttaagtg atctgtgaca tttttaatgt ttctatttca    2460
tacgtgcctt tgtgattgctg ctgctgtgag ggtacactcc tgtcggggaa aagtctgttt    2520
tggtttggtt tttaatgaaa taaaccctcca agagcttaca ttcctgaaaa aaaaaaaaa    2580
```

<210> SEQ ID NO 24
<211> LENGTH: 473
<212> TYPE: PRT
<213> ORGANISM: Homo sapiens

<400> SEQUENCE: 24

```
Met Ala Thr Ala Thr Glu Gln Trp Val Leu Val Glu Met Val Gln Ala
1               5                   10                  15

Leu Tyr Glu Ala Pro Ala Tyr His Leu Ile Leu Glu Gly Ile Leu Ile
                20                  25                  30

Leu Trp Ile Ile Arg Leu Leu Phe Ser Lys Thr Tyr Lys Leu Gln Glu
            35                  40                  45

Arg Ser Asp Leu Thr Val Lys Glu Lys Glu Glu Leu Ile Glu Glu Trp
    50                  55                  60

Gln Pro Glu Pro Leu Val Pro Val Pro Lys Asp His Pro Ala Leu
65                  70                  75                  80

Asn Tyr Asn Ile Val Ser Gly Pro Pro Ser His Lys Thr Val Val Asn
                85                  90                  95

Gly Lys Glu Cys Ile Asn Phe Ala Ser Phe Asn Phe Leu Gly Leu Leu
            100                 105                 110

Asp Asn Pro Arg Val Lys Ala Ala Ala Leu Ala Ser Leu Lys Lys Tyr
        115                 120                 125

Gly Val Gly Thr Cys Gly Pro Arg Gly Phe Tyr Gly Thr Phe Asp Val
    130                 135                 140

His Leu Asp Leu Glu Asp Arg Leu Ala Lys Phe Met Lys Thr Glu Glu
145                 150                 155                 160

Ala Ile Ile Tyr Ser Tyr Gly Phe Ala Thr Ile Ala Ser Ala Ile Pro
                165                 170                 175

Ala Tyr Ser Lys Arg Gly Asp Ile Val Phe Val Asp Arg Ala Ala Cys
            180                 185                 190

Phe Ala Ile Gln Lys Gly Leu Gln Ala Ser Arg Ser Asp Ile Lys Leu
        195                 200                 205

Phe Lys His Asn Asp Met Ala Asp Leu Glu Arg Leu Leu Lys Glu Gln
    210                 215                 220

Glu Ile Glu Asp Gln Lys Asn Pro Arg Lys Ala Arg Val Thr Arg Arg
225                 230                 235                 240

Phe Ile Val Val Glu Gly Leu Tyr Met Asn Thr Gly Thr Ile Cys Pro
                245                 250                 255

Leu Pro Glu Leu Val Lys Leu Lys Tyr Lys Tyr Lys Ala Arg Ile Phe
            260                 265                 270

Leu Glu Glu Ser Leu Ser Phe Gly Val Leu Gly Glu His Gly Arg Gly
        275                 280                 285

Val Thr Glu His Tyr Gly Ile Asn Ile Asp Asp Ile Asp Leu Ile Ser
    290                 295                 300

Ala Asn Met Glu Asn Ala Leu Ala Ser Ile Gly Gly Phe Cys Cys Gly
305                 310                 315                 320

Arg Ser Phe Val Ile Asp His Gln Arg Leu Ser Gly Gln Gly Tyr Cys
                325                 330                 335

Phe Ser Ala Ser Leu Pro Pro Leu Leu Ala Ala Ala Ile Glu Ala
            340                 345                 350

Leu Asn Ile Met Glu Glu Asn Pro Gly Ile Phe Ala Val Leu Lys Glu
        355                 360                 365

Lys Cys Gly Gln Ile His Lys Ala Leu Gln Gly Ile Ser Gly Leu Lys
    370                 375                 380
```

```
Val Val Gly Glu Ser Leu Ser Pro Ala Phe His Leu Gln Leu Glu Glu
385                 390                 395                 400

Ser Thr Gly Ser Arg Glu Gln Asp Val Arg Leu Leu Gln Glu Ile Val
                405                 410                 415

Asp Gln Cys Met Asn Arg Ser Ile Ala Leu Thr Gln Ala Arg Tyr Leu
            420                 425                 430

Glu Lys Glu Glu Lys Cys Leu Pro Pro Ser Ile Arg Val Val Val
        435                 440                 445

Thr Val Glu Gln Thr Glu Glu Leu Glu Arg Ala Ala Ser Thr Ile
    450                 455                 460

Lys Glu Val Ala Gln Ala Val Leu Leu
465                 470

<210> SEQ ID NO 25
<211> LENGTH: 473
<212> TYPE: PRT
<213> ORGANISM: Mus musculus

<400> SEQUENCE: 25

Met Ala Thr Val Ala Glu Gln Trp Val Leu Val Glu Met Val Gln Ala
1               5                   10                  15

Leu Tyr Glu Ala Pro Ala Tyr His Leu Ile Leu Glu Gly Ile Leu Ile
            20                  25                  30

Leu Trp Ile Ile Arg Leu Val Phe Ser Lys Thr Tyr Lys Leu Gln Glu
        35                  40                  45

Arg Ser Asp Leu Thr Ala Lys Glu Lys Glu Glu Leu Ile Glu Glu Trp
    50                  55                  60

Gln Pro Glu Pro Leu Val Pro Pro Val Ser Lys Asn His Pro Ala Leu
65                  70                  75                  80

Asn Tyr Asn Ile Val Ser Gly Pro Pro Thr His Asn Ile Val Val Asn
                85                  90                  95

Gly Lys Glu Cys Val Asn Phe Ala Ser Phe Asn Phe Leu Gly Leu Leu
            100                 105                 110

Ala Asn Pro Arg Val Lys Ala Thr Ala Phe Ser Ser Leu Lys Lys Tyr
        115                 120                 125

Gly Val Gly Thr Cys Gly Pro Arg Gly Phe Tyr Gly Thr Phe Asp Val
    130                 135                 140

His Leu Asp Leu Glu Glu Arg Leu Ala Lys Phe Met Lys Thr Glu Glu
145                 150                 155                 160

Ala Ile Ile Tyr Ser Tyr Gly Phe Ser Thr Ile Ala Ser Ala Ile Pro
                165                 170                 175

Ala Tyr Ser Lys Arg Gly Asp Ile Ile Phe Val Asp Ser Ala Ala Cys
            180                 185                 190

Phe Ala Ile Gln Lys Gly Leu Gln Ala Ser Arg Ser Asp Ile Lys Leu
        195                 200                 205

Phe Lys His Asn Asp Val Ala Asp Leu Glu Arg Leu Leu Lys Glu Gln
    210                 215                 220

Glu Ile Glu Asp Gln Lys Asn Pro Arg Lys Ala Arg Val Thr Arg Arg
225                 230                 235                 240

Phe Ile Val Val Glu Gly Leu Tyr Met Asn Thr Gly Thr Ile Cys Pro
                245                 250                 255

Leu Pro Glu Leu Val Lys Leu Lys Tyr Lys Tyr Lys Ala Arg Ile Phe
            260                 265                 270
```

```
Leu Glu Glu Ser Leu Ser Phe Gly Val Leu Glu His Gly Arg Gly
        275                 280                 285
Val Thr Glu His Tyr Gly Ile Ser Ile Asp Asp Ile Asp Leu Ile Ser
    290                 295                 300
Ala Asn Met Glu Asn Ala Leu Ala Ser Val Gly Gly Phe Cys Cys Gly
305                 310                 315                 320
Arg Ser Phe Val Val Asp His Gln Arg Leu Ser Gly Gln Gly Tyr Cys
                325                 330                 335
Phe Ser Ala Ser Leu Pro Pro Leu Leu Ala Ala Ala Ile Glu Ala
            340                 345                 350
Leu Asn Ile Met Glu Glu Asn Pro Asp Ile Phe Ala Val Leu Lys Lys
        355                 360                 365
Lys Cys Gln Asn Ile His Lys Ser Leu Gln Gly Val Ser Gly Leu Lys
    370                 375                 380
Val Val Gly Glu Ser Leu Ser Pro Ala Leu His Leu Gln Leu Glu Glu
385                 390                 395                 400
Ser Thr Gly Ser Arg Glu Lys Asp Val Lys Leu Leu Gln Ala Ile Val
                405                 410                 415
Asp Gln Cys Met Asp Lys Gly Ile Ala Leu Thr Gln Ala Arg Tyr Leu
            420                 425                 430
Asp Lys Glu Glu Lys Cys Leu Pro Pro Pro Ser Ile Arg Val Val Val
        435                 440                 445
Thr Val Glu Gln Thr Glu Glu Leu Gln Arg Ala Ala Ser Thr Ile
    450                 455                 460
Arg Glu Ala Ala Gln Ala Val Leu Leu
465                 470
```

<210> SEQ ID NO 26
<211> LENGTH: 73
<212> TYPE: RNA
<213> ORGANISM: Artificial Sequence
<220> FEATURE:
<223> OTHER INFORMATION: Synthetic Polynucleotide

<400> SEQUENCE: 26
ugcuguuuag aguacgcagg aaucgcguuu uggccacuga cugacugacg cgauucccgu    60
acucuaaaca gca                                                      73

<210> SEQ ID NO 27
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 27
tttccaccat agccagtgcg attcctgcgt actctaaaag aggggacatg tttt          54

<210> SEQ ID NO 28
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 28
aaaggtggta tcggtcacgc taaggacgca tgagattttc tcccctgtaa caaaa         55

```
<210> SEQ ID NO 29
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 29
ttgccaccat agccagtgct attcctgctt actctaaaag aggggacatt gtttt         55

<210> SEQ ID NO 30
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 30
aacggtggta tcggtcacga taaggacgaa tgagattttc tccctgtaa caaaa          55

<210> SEQ ID NO 31
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 31

Phe Ser Thr Ile Ala Ser Ala Ile Pro Ala Tyr Ser Lys Arg Gly Asp
1               5                   10                  15

Ile Val Phe

<210> SEQ ID NO 32
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 32

Phe Ala Thr Ile Ala Ser Ala Ile Pro Ala Tyr Ser Lys Arg Gly Asp
1               5                   10                  15

Ile Val Phe

<210> SEQ ID NO 33
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 33

Ala Ile Pro Ala Tyr Ser Lys
1               5
```